(12) United States Patent
Uchitel et al.

(10) Patent No.: US 9,730,773 B2
(45) Date of Patent: *Aug. 15, 2017

(54) BONE GRAFT INJECTION METHODS

(71) Applicant: Maxillent Ltd., Herzliya (IL)

(72) Inventors: Ilan Uchitel, Herzliya (IL); Adi Alphandary, Herzliya (IL); Gideon Fostick, Herzliya (IL); Yossi Gross, Herzliya (IL); Zev Sohn, Herzliya (IL)

(73) Assignee: Maxillent Ltd., Herzliya (IL)

( * ) Notice: Subject to any disclaimer, the term of this patent is extended or adjusted under 35 U.S.C. 154(b) by 172 days.

This patent is subject to a terminal disclaimer.

(21) Appl. No.: 14/707,688

(22) Filed: May 8, 2015

(65) Prior Publication Data
US 2016/0310192 A1    Oct. 27, 2016

Related U.S. Application Data

(60) Provisional application No. 62/150,969, filed on Apr. 22, 2015.

(51) Int. Cl.
*A61B 17/88* (2006.01)
*A61C 8/00* (2006.01)
(Continued)

(52) U.S. Cl.
CPC ........ *A61C 8/0092* (2013.01); *A61B 17/8808* (2013.01); *A61B 17/8811* (2013.01); *A61B 17/8816* (2013.01); *A61B 17/8822* (2013.01); *A61B 17/8827* (2013.01); *A61C 1/0084* (2013.01); *A61C 1/0092* (2013.01); *A61C 8/0006* (2013.01); *A61C 17/0202* (2013.01);
(Continued)

(58) Field of Classification Search
CPC ............................ A61B 174/8802–2017/8844
See application file for complete search history.

(56) References Cited

U.S. PATENT DOCUMENTS 2,347,567 A    4/1944 Kresse
2,436,623 A    2/1948 Zile
(Continued)

FOREIGN PATENT DOCUMENTS

CN    1125559    7/1996
DE    4321785    3/1995
(Continued)

OTHER PUBLICATIONS

An International Search Report and Written Opinion for International Application No. PCT/IL2016/050423, mailed Oct. 27, 2016, 18 pages.

(Continued)

*Primary Examiner* — Zade Coley
(74) *Attorney, Agent, or Firm* — Fish & Richardson P.C.

(57) ABSTRACT

A method is provided that includes injecting, from a first side of a bone, through (a) exactly one bore that passes through the bone from the first side to a second side of the bone, and (b) into a cavity adjacent to the second side of the bone, a solid-liquid composition of solid particles and a physiological liquid solution. The physiological liquid solution is drained from the cavity and through the bore while passage of the solid particles of the solid-liquid composition is inhibited, such that the solid particles accumulate in the cavity.

13 Claims, 22 Drawing Sheets

(51) Int. Cl.
  *A61C 1/00* (2006.01)
  *A61C 8/02* (2006.01)
  *A61C 17/02* (2006.01)
  *A61C 17/14* (2006.01)

(52) U.S. Cl.
  CPC ...... *A61C 17/14* (2013.01); *A61B 2017/8813* (2013.01)

(56) References Cited

U.S. PATENT DOCUMENTS

| | | | |
|---|---|---|---|
| 3,543,784 A * | 12/1970 | Smith | G05D 7/03 137/487 |
| 3,659,881 A | 5/1972 | Tinsley et al. | |
| 3,875,595 A | 4/1975 | Froning | |
| 3,905,109 A * | 9/1975 | Cohen | A61C 8/0022 433/174 |
| 4,021,921 A | 5/1977 | Detaille | |
| 4,112,944 A | 9/1978 | Williams | |
| 4,313,434 A | 2/1982 | Segal | |
| 4,412,825 A | 11/1983 | Tokarz | |
| 4,416,629 A | 11/1983 | Mozsary et al. | |
| 4,431,416 A | 2/1984 | Niznick | |
| 4,445,509 A | 5/1984 | Auth | |
| 4,473,353 A | 9/1984 | Greggs | |
| 4,521,192 A | 6/1985 | Linkow | |
| 4,523,910 A | 6/1985 | Makovich | |
| 4,665,918 A | 5/1987 | Garza | |
| 4,673,353 A | 6/1987 | Nevin | |
| 4,690,672 A | 9/1987 | Veltrup | |
| 4,690,684 A | 9/1987 | McGreevy | |
| 4,729,763 A | 3/1988 | Henrie | |
| 4,740,207 A | 4/1988 | Kreamer | |
| 4,744,754 A | 5/1988 | Ross | |
| 4,768,507 A | 9/1988 | Fischell | |
| 4,787,906 A | 11/1988 | Haris | |
| 4,824,436 A | 4/1989 | Wolinsky | |
| 4,832,688 A | 5/1989 | Sagae | |
| 4,843,112 A | 6/1989 | Gerhart | |
| 4,854,872 A | 8/1989 | Detsch | |
| 4,863,472 A | 9/1989 | Tormala | |
| 4,878,906 A | 11/1989 | Lindemann | |
| 4,902,276 A | 2/1990 | Zakko | |
| 4,922,905 A | 5/1990 | Strecker | |
| 4,950,227 A | 8/1990 | Savin | |
| 4,960,381 A | 10/1990 | Niznick | |
| 4,969,888 A | 11/1990 | Scholten | |
| 4,994,298 A | 2/1991 | Yasuda | |
| 5,022,857 A | 6/1991 | Matsutani et al. | |
| 5,047,030 A | 9/1991 | Draenert | |
| 5,049,125 A | 9/1991 | Accaries et al. | |
| 5,078,605 A | 1/1992 | Sutter et al. | |
| 5,108,404 A | 4/1992 | Scholten | |
| 5,108,416 A | 4/1992 | Ryan | |
| 5,135,484 A | 8/1992 | Wright | |
| 5,146,933 A | 9/1992 | Boyd | |
| 5,158,548 A | 10/1992 | Lau | |
| 5,188,488 A | 2/1993 | Nakayama et al. | |
| 5,192,307 A | 3/1993 | Wall | |
| 5,234,457 A | 8/1993 | Andersen | |
| 5,242,399 A | 9/1993 | Lau | |
| 5,254,089 A | 10/1993 | Wang | |
| 5,261,818 A | 11/1993 | Shaw | |
| 5,284,688 A | 2/1994 | Hiatt | |
| 5,291,914 A | 3/1994 | Bares et al. | |
| 5,306,286 A | 4/1994 | Stack | |
| 5,312,255 A | 5/1994 | Bauer | |
| 5,366,374 A | 11/1994 | Vlassis | |
| 5,370,609 A | 12/1994 | Drasler et al. | |
| 5,405,322 A | 4/1995 | Lennox | |
| 5,423,885 A | 6/1995 | Williams | |
| 5,439,446 A | 8/1995 | Barry | |
| 5,441,515 A | 8/1995 | Khosravi | |
| 5,443,500 A | 8/1995 | Sigwart | |
| 5,456,601 A | 10/1995 | Sendax | |
| 5,481,260 A | 1/1996 | Buckler et al. | |
| 5,496,368 A | 3/1996 | Wiese | |
| 5,536,242 A | 7/1996 | Willard et al. | |
| 5,549,676 A | 8/1996 | Johnson | |
| 5,549,679 A | 8/1996 | Kuslich | |
| 5,562,736 A | 10/1996 | Ray | |
| 5,571,189 A | 11/1996 | Kuslich | |
| 5,575,650 A | 11/1996 | Niznick et al. | |
| 5,584,688 A | 12/1996 | Sakuma et al. | |
| 5,638,046 A | 6/1997 | Malinowski | |
| 5,674,295 A | 10/1997 | Ray | |
| 5,685,716 A | 11/1997 | Linkow | |
| 5,695,338 A | 12/1997 | Robert | |
| 5,711,315 A * | 1/1998 | Jerusalmy | A61B 17/0218 128/898 |
| 5,741,223 A | 4/1998 | Janzen | |
| 5,746,762 A | 5/1998 | Bass | |
| 5,759,036 A | 6/1998 | Hinds | |
| 5,782,918 A | 7/1998 | Klardie et al. | |
| 5,792,400 A | 8/1998 | Talja | |
| 5,795,160 A | 8/1998 | Hahn et al. | |
| 5,827,289 A | 10/1998 | Reiley | |
| 5,829,977 A | 11/1998 | Rogers et al. | |
| 5,839,899 A | 11/1998 | Robinson | |
| 5,843,022 A | 12/1998 | Willard et al. | |
| 5,857,998 A | 1/1999 | Barry | |
| 5,868,572 A | 2/1999 | Lazzara et al. | |
| 5,879,161 A | 3/1999 | Lazzara | |
| 5,882,353 A | 3/1999 | VanBeek | |
| 5,915,967 A | 6/1999 | Clokie | |
| 5,919,234 A | 7/1999 | Lemperle | |
| 5,944,686 A | 8/1999 | Patterson et al. | |
| 5,967,777 A | 10/1999 | Klein et al. | |
| 5,972,015 A | 10/1999 | Scribner | |
| 5,989,025 A | 11/1999 | Conley | |
| 6,027,744 A | 2/2000 | Vacanti | |
| 6,045,497 A | 4/2000 | Schweich | |
| 6,068,479 A | 5/2000 | Kwan | |
| 6,077,076 A | 6/2000 | Comfort | |
| 6,127,597 A | 10/2000 | Beyar | |
| 6,159,161 A | 12/2000 | Hodosh | |
| 6,200,289 B1 | 3/2001 | Hochman et al. | |
| 6,206,930 B1 | 3/2001 | Burg | |
| 6,214,012 B1 | 4/2001 | Karpman | |
| 6,220,860 B1 | 4/2001 | Hansson | |
| 6,264,695 B1 | 7/2001 | Stoy | |
| 6,270,346 B1 | 8/2001 | Grabenhofer et al. | |
| 6,273,720 B1 | 8/2001 | Spalten | |
| 6,506,214 B1 | 1/2003 | Gross | |
| 6,511,493 B1 | 1/2003 | Moutafis et al. | |
| 6,616,698 B2 | 9/2003 | Scarborough | |
| 6,689,089 B1 | 2/2004 | Tiedtke et al. | |
| 6,740,093 B2 | 5/2004 | Hochschuler | |
| 6,758,673 B2 | 7/2004 | Fromovich et al. | |
| 6,827,575 B1 | 12/2004 | Jorneus | |
| 6,939,135 B2 | 9/2005 | Sapian | |
| 7,100,476 B1 | 9/2006 | Feit | |
| 7,122,017 B2 | 10/2006 | Moutafis et al. | |
| 7,217,130 B2 | 5/2007 | Giorno | |
| 7,297,102 B2 | 11/2007 | Smith et al. | |
| 7,300,282 B2 | 11/2007 | Sapian | |
| 7,364,430 B2 | 4/2008 | Kitamura et al. | |
| 7,396,232 B2 | 7/2008 | Fromovich et al. | |
| 7,510,397 B2 * | 3/2009 | Hochman | A61C 8/0033 433/172 |
| 7,771,482 B1 | 8/2010 | Karmon | |
| 7,934,929 B2 * | 5/2011 | Better | A61C 8/0018 433/173 |
| 8,029,284 B2 | 10/2011 | Better et al. | |
| 8,356,994 B2 | 1/2013 | Better et al. | |
| 8,388,343 B2 | 3/2013 | Better et al. | |
| 8,556,627 B2 | 10/2013 | Better et al. | |
| 8,622,739 B2 | 1/2014 | Karmon | |
| 8,662,891 B2 | 3/2014 | Uchitel et al. | |
| 8,696,354 B2 | 4/2014 | Fostick et al. | |
| 8,721,334 B2 | 5/2014 | Better et al. | |
| 2002/0188307 A1 | 12/2002 | Pintor et al. | |
| 2003/0004459 A1 | 1/2003 | McKendry et al. | |

(56) References Cited

U.S. PATENT DOCUMENTS

| | | | |
|---|---|---|---|
| 2003/0105469 A1* | 6/2003 | Karmon | A61B 17/58 606/92 |
| 2003/0175656 A1 | 9/2003 | Livne et al. | |
| 2003/0228556 A1 | 12/2003 | Giorno | |
| 2003/0232308 A1 | 12/2003 | Simmons | |
| 2004/0018471 A1 | 1/2004 | Giorno | |
| 2005/0105385 A1* | 5/2005 | McGill | A61B 17/8805 366/139 |
| 2005/0187613 A1 | 8/2005 | Bolduc | |
| 2006/0020326 A9 | 1/2006 | Bolduc et al. | |
| 2006/0084034 A1* | 4/2006 | Hochman | A61C 8/0033 433/173 |
| 2006/0142630 A1 | 6/2006 | Meretei | |
| 2006/0172255 A1 | 8/2006 | Hochman et al. | |
| 2006/0210949 A1 | 9/2006 | Stoop | |
| 2007/0055257 A1 | 3/2007 | Vaccaro et al. | |
| 2007/0161943 A1* | 7/2007 | Lidgren | A61B 17/1615 604/19 |
| 2007/0162024 A1 | 7/2007 | Siemonsmeier | |
| 2007/0238068 A1 | 10/2007 | Comfortes | |
| 2008/0108011 A1* | 5/2008 | Nahlieli | A61B 1/247 433/29 |
| 2008/0161840 A1 | 7/2008 | Osiroff et al. | |
| 2008/0161934 A1* | 7/2008 | Yamada | A61B 17/1655 623/17.17 |
| 2008/0182225 A1 | 7/2008 | Gordils | |
| 2008/0213729 A1 | 9/2008 | Hochman | |
| 2008/0215010 A1 | 9/2008 | Silver et al. | |
| 2008/0293010 A1 | 11/2008 | Song | |
| 2008/0319466 A1* | 12/2008 | Eder | A61C 8/0092 606/169 |
| 2009/0136898 A1 | 5/2009 | Kim | |
| 2009/0142731 A1* | 6/2009 | Kim | A61C 3/02 433/165 |
| 2009/0186317 A1 | 7/2009 | Allon | |
| 2009/0239200 A1 | 9/2009 | Brajnovic et al. | |
| 2009/0259227 A1 | 10/2009 | Ahn et al. | |
| 2009/0326537 A1 | 12/2009 | Anderson | |
| 2010/0047733 A1 | 2/2010 | Nahlieli | |
| 2010/0081111 A1 | 4/2010 | Better et al. | |
| 2010/0081112 A1* | 4/2010 | Better | A61C 8/0018 433/174 |
| 2010/0196841 A1* | 8/2010 | Nahlieli | A61B 1/247 433/29 |
| 2010/0196844 A1 | 8/2010 | Heo | |
| 2010/0255446 A1* | 10/2010 | Better | A61C 8/0018 433/174 |
| 2010/0266984 A1 | 10/2010 | Jung | |
| 2010/0324561 A1 | 12/2010 | Watzek et al. | |
| 2010/0324644 A1 | 12/2010 | Levi et al. | |
| 2011/0008746 A1* | 1/2011 | Kim | A61C 8/0006 433/25 |
| 2011/0082417 A1* | 4/2011 | Lidgren | A61B 17/1615 604/28 |
| 2011/0111364 A1 | 5/2011 | Haber | |
| 2011/0144449 A1* | 6/2011 | Ortiz | A61B 17/3421 600/216 |
| 2011/0165536 A1 | 7/2011 | Better et al. | |
| 2011/0212415 A1 | 9/2011 | Better et al. | |
| 2011/0287386 A1 | 11/2011 | Better et al. | |
| 2011/0318707 A1 | 12/2011 | Better et al. | |
| 2012/0094254 A1 | 4/2012 | Uchitel | |
| 2012/0164603 A1 | 6/2012 | Better et al. | |
| 2013/0149669 A1 | 6/2013 | Fostick et al. | |
| 2013/0150857 A1 | 6/2013 | Better et al. | |
| 2014/0106296 A1 | 4/2014 | Woodard et al. | |
| 2014/0147809 A1 | 5/2014 | Uchitel et al. | |
| 2014/0329197 A1 | 11/2014 | Bassett et al. | |
| 2016/0310242 A1 | 10/2016 | Uchitel et al. | |
| 2016/0310243 A1 | 10/2016 | Uchitel et al. | |

FOREIGN PATENT DOCUMENTS

| | | | |
|---|---|---|---|
| DE | 10 2007 059226 | 6/2008 | |
| EP | 0411767 | 6/1991 | |
| EP | 0489496 | 6/1992 | |
| EP | 1195146 | 10/2000 | |
| EP | 1110509 | 6/2001 | |
| EP | 1174094 | 1/2002 | |
| EP | 1145689 | 6/2003 | |
| FR | 2516784 | 11/1981 | |
| FR | 2906708 | 11/2006 | |
| IL | 212022 | 8/2013 | |
| IL | 214635 | 10/2013 | |
| IL | WO 2013157000 A1 * | 10/2013 | ............ A61C 5/02 |
| JP | H06-178784 | 6/1994 | |
| JP | H07-16231 | 1/1995 | |
| WO | WO 96/24310 | 8/1996 | |
| WO | WO 01/85062 | 11/2001 | |
| WO | 2004/054461 | 7/2004 | |
| WO | 2007/007331 | 1/2007 | |
| WO | 2007/080595 | 7/2007 | |
| WO | 2007/114553 | 10/2007 | |
| WO | WO 2008/029215 | 3/2008 | |
| WO | 2008/081423 | 7/2008 | |
| WO | 2009/062225 | 5/2009 | |
| WO | 2010/035270 | 4/2010 | |
| WO | 2010/146573 | 12/2010 | |
| WO | 2013/157000 | 10/2013 | |
| WO | 2014/199332 | 12/2014 | |

OTHER PUBLICATIONS

An Invitation to Pay Additional Fees for International Application No. PCT/IL2016/050423, mailed Sep. 1, 2016, 9 pages.

U.S. Appl. No. 60/619,542, filed Oct. 15, 2004, Hochman.

U.S. Appl. No. 62/150,969, filed Apr. 22, 2015, Uchitel et al.

An English Translation of an Office Action dated Feb. 11, 2014, which issued during the prosecution of Chinese Patent Application No. 201080026484.7.

An English Translation of an Office Action dated Jan. 28, 2014, which issued during the prosecution of Chinese Patent Application No. 20090147751.3.

An English Translation of an Office Action dated Jul. 30, 2013, which issued during the prosecution of Chinese Patent Application No. 200980147751.3.

An International Search Report and a Written Opinion both dated Sep. 23, 2014, which issued during the prosecution of Applicant's PCT/IB2014/062168.

An International Preliminary Report on Patentability dated Dec. 29, 2011, which issued during the prosecution of Applicant's PCT/IL2010/000252.

An International Preliminary Report on Patentability dated Mar. 29, 2011, which issued during the prosecution of Applicant's PCT/IL2009/000931.

An International Search Report and a Written Opinion both dated Mar. 23, 2010, which issued during the prosecution of Applicant's PCT/IL09/00931.

An International Search Report dated Jul. 15, 2010, which issued during the prosecution of Applicant's PCT/IL2010/000252.

An Office Action dated Apr. 11, 2011, which issued during the prosecution of U.S. Appl. No. 12/485,199.

An Office Action dated Dec. 27, 2011, which issued during the prosecution of U.S. Appl. No. 12/661,795.

An Office Action dated Jul. 11, 2014, which issued during the prosecution of U.S. Appl. No. 14/086,910.

An Office Action dated Jun. 20, 2013, which issued during the prosecution of U.S. Appl. No. 13/196,632.

An Office Action dated Jun. 24, 2013, which issued during the prosecution of U.S. Appl. No. 13/314,818.

An Office Action dated Jun. 26, 2013, which issued during the prosecution of U.S. Appl. No. 13/409,631.

An Office Action dated Jun. 26, 2013, which issued during the prosecution of U.S. Appl. No. 13/760,206.

(56) References Cited

OTHER PUBLICATIONS

An Office Action dated Jun. 28, 2012, which issued during the prosecution of U.S. Appl. No. 13/040,440.
An Office Action dated Mar. 15, 2013, which issued during the prosecution of U.S. Appl. No. 13/196,632.
An Office Action dated Mar. 19, 2013, which issued during the prosecution of U.S. Appl. No. 13/409,631.
An Office Action dated Mar. 29, 2013, which issued during the prosecution of U.S. Appl. No. 13/228,564.
An Office Action dated Oct. 1, 2010, which issued during the prosecution of U.S. Appl. No. 12/240,353.
An Office Action dated Oct. 16, 2012, which issued during the prosecution of U.S. Appl. No. 12/661,795.
Branemark System® product description, Nobel Biocare™ AB (Zurich, Switzerland) (downloaded from http://www1.nobelbiocare.com/en/implants-and-abutments/products/parallelled-walled-implants/Branemark-system.aspx on Mar. 12, 2010).
Bui, "Guided Bone Regeneration," Dec. 19, 2011, downloaded from http://www.drbui.com/artgbr.html.
Chen et al., "An 8-year retrospective study: 1,100 patients receiving 1,557 implants using the minimally invasive hydraulic sinus condensing technique," J Periodontol, 2005, 76:482-493.
European Search Report dated Jan. 24, 2014, which issued during the prosecution of Applicant's European App. No. 09815774.6.
European Search Report dated Nov. 4, 2013 which issued during the prosecution of Applicant's European App No. 10789099.
Flanagan, "Important arterial supply of the mandible, control of an arterial hemorrhage, and report of a hemorrhagic incident," J Oral Implantol, 2003, 29(4): 165-73.
Fritz et al., "The use of Guided Bone Regeneration to fill Large Mandibular Defects in Monkeys," A Pilot Study, Jun. 1994, JOMI, 644-652.
Givol et al., "Emergency Tracheostomy Following Life-Threatening Hemorrhage in the Floor of the Mouth During Immediate Implant Placement in the Mandibular Canine Region," J Periodontol, Dec. 2000, 1893-1895.
Holmquist et al., "A new technique for reconstruction of the atrophied narrow alveolar crest in the maxilla using morselized impacted bone allograft and later placement of dental implants," Clinical Implant Dentistry and Related Research 10, Online publication date: May 1, 2008 (Abstract).
Isaacson, "Sublinigual hematoma formation during immediate placement of mandibular endosseous implants," J Am Dent Assoc, 2004, 1335: 168-172.
Kawana et al., "Acquisition of Bone Structure in Drilling process using Cutting force Estimation," The 8th France-Japan and 6th Europe-Asia Congress on Mechatronics, Nov. 2010, 393-398, Yokohama, Japan.
Lee et al., "Crestal Sinus Lift: A Minimally Invasive and Systematic Approach to Sinus Grafting," The Journal of Implant & Advanced Clinical Dentistry 1(1), Mar. 2009.
Muronoi et al., "Simplified procedure for augmentation of the sinus floor using a haemostatic nasal balloon," British Journal of Oral & Maxillofacial Surgery, 2003, 41(2): 120-121.
NobelActive™ External Connection product catalog, Nobel Biocare™ AB (Zurich, Switzerland), 2007, 48 pages.
Notice of Allowance dated Dec. 27, 2013, which issued during the prosecution of U.S. Appl. No. 13/196,632.
Notice of Allowance dated Jan. 6, 2011, which issued during the prosecution of U.S. Appl. No. 12/240,353.
Notice of Allowance dated Jun. 25, 2013, which issued during the prosecution of U.S. Appl. No. 13/228,564.
Notice of Allowance dated Jun. 27, 2011, which issued during the prosecution of U.S. Appl. No. 12/485,199.
Notice of Allowance dated Nov. 15, 2013, which issued during the prosecution of U.S. Appl. No. 12/661,795.
Notice of Allowance dated Nov. 25, 2013, which issued during the prosecution of U.S. Appl. No. 13/314,740.
Notice of Allowance dated Nov. 25, 2013, which issued during the prosecution of U.S. Appl. No. 13/409,631.
Notice of Allowance dated Oct. 11, 2013, which issued during the prosecution of U.S. Appl. No. 13/314,818.
Notice of Allowance dated Sep. 24, 2012, which issued during the prosecution of U.S. Appl. No. 13/040,440.
Office Action dated Jul. 2, 2013 together with an English Translation of the Office Action (the relevant part only), which issued during the prosecution of Israel Patent Application No. 214043.
Pjetursson et al., "Maxillary sinus floor elevation using the (transalveolar) osteotome technique with or without grafting material. Part I: implant survival and patients' perception," Clin Oral Impl Res, 2009, 20: 667-676.
Restriction Requirement dated Oct. 9, 2013, which issued during the prosecution of U.S. Appl. No. 13/314,740.
Riley et al., "The Episure syringe: a novel loss of resistance syringe for locating the epidural space," Anesth Analg., Oct. 2007, 105(4): 1164-6.
SinCrest brochure, Meta Advanced Medical Technology C.G.M. S.p.A. (Reggio Emilia, Italy) (downloaded Sep. 1, 2008), 2 pages.
Sinus Lift Kit brochure, Cowellmedi USA Inc. (Buena Park, CA, USA) received on Mar. 15, 2011, 10 pages.
Sotirakis, "A different method for elevation of the floor of the maxillary sinus: Experimental study and reference to some cases," Mediterranean Dental Implant Congress (Athens, Greece), Scientific Programme MDIC (2004). Abstract only.
Vercellotti et al., "The Piezoelectic Bony Window Osteotomy and Sinus Membrane Elevation: Introduction of a New Technique for Simplification of the Sinus Augmentation Procedure," Int J Periodontics Restorative Dent, 2001, 21(6): 561-7.
Vercellotti, "Piezoelectric surgery in implantology: a case report—a new piezoelectric ridge expansion technique," Int J Periodontics Restorative Dent, 2000, 20(4): 358-65.
Zimmer ERA™ Mini Dental Implant System Product Catalog, Zimmer Dental Inc. (Carlsbad, CA, USA) (Feb. 2010), 8 pages.
Zimmer ERA™ Mini Dental Implant System Usage Guide, Zimmer Dental (Carlsbad, CA) (Dec. 2009), 9 pages.
Zimmer Spline® Implant System Product Catalog, Zimmer Dental Inc. (Carlsbad, CA, USA) (Feb. 2007), 36 pages.
Zimmer SwissPlus® Implant System Product Catalog, Zimmer Dental Inc. (Carlsbad, CA, USA) (Jan. 2007), 32 pages.
Zimmer Tapered Screw-Vent® Implant System product catalog, Zimmer Dental Inc. (Carlsbad, CA, USA) (2008), 91 pages.
Zimmer Tapered Screw-Vent® Implant System Product Catalog, Zimmer Dental Inc. (Carlsbad, CA, USA) (Mar. 2009), 68 pages.
Non-Final Office Action for U.S. Appl. No. 14/710,388, dated Dec. 13, 2016, 11 pages.
Non-Final Office Action for U.S. Appl. No. 14/1710,404 dated Dec. 21, 2016, 10 pages.
The extended European Search Report for EP16196581.9 dated Jan. 2, 2017, 7 pages.
Notice of Allowance for U.S. Appl. No. 14/710,388, dated Apr. 5, 2017, 8 pages.
Notice of Allowance for U.S. Appl. No. 14/710,404, dated Apr. 11, 2017, 9 pages.

* cited by examiner

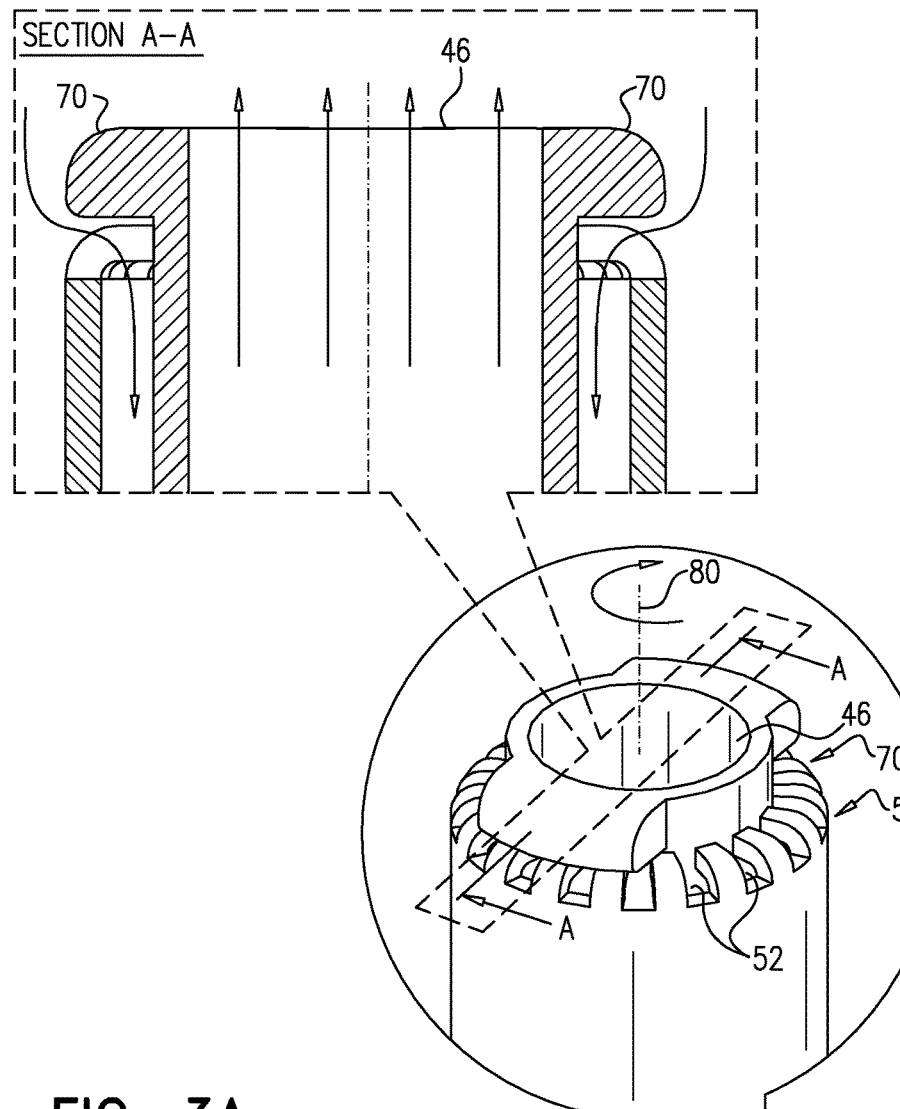
FIG. 3A
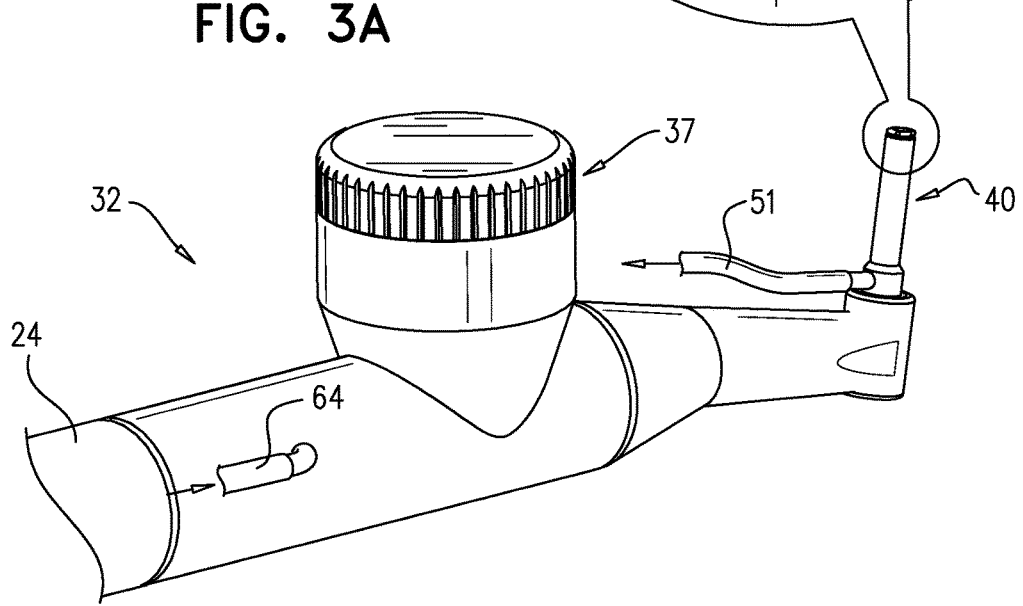

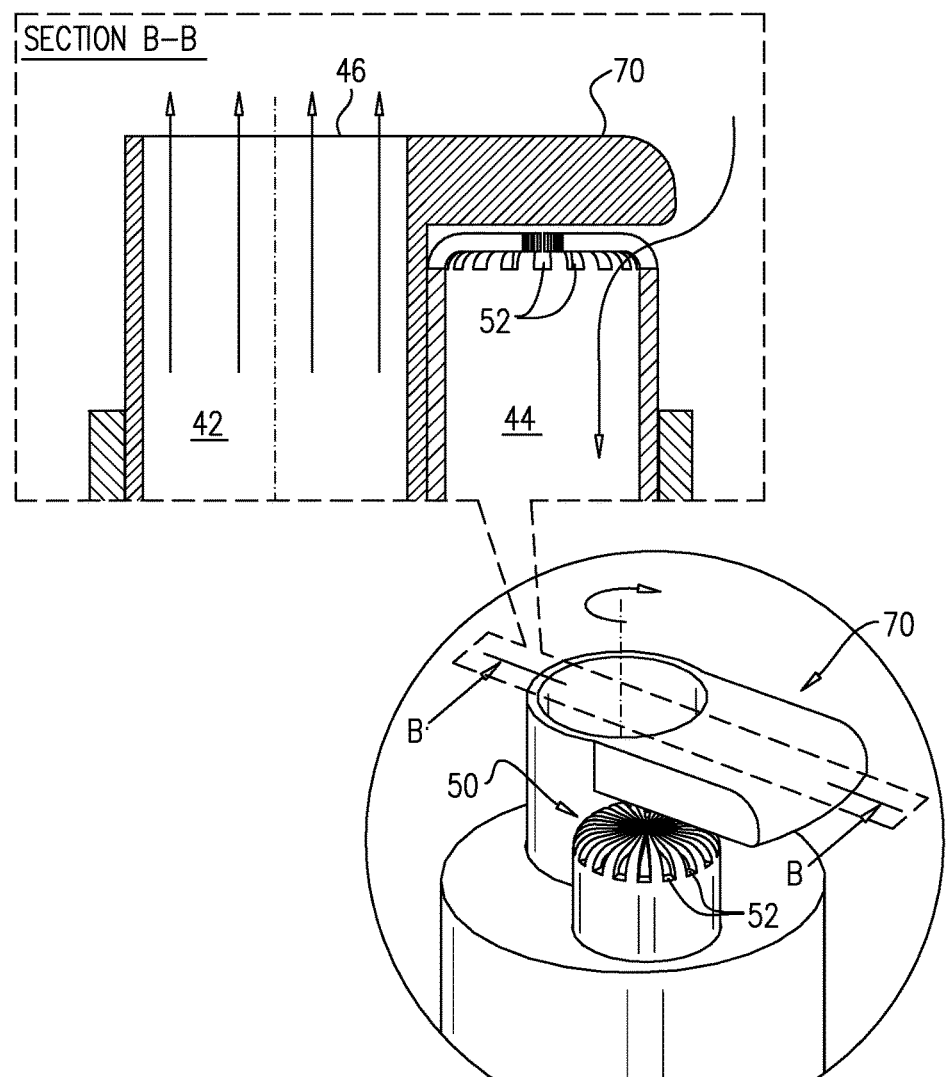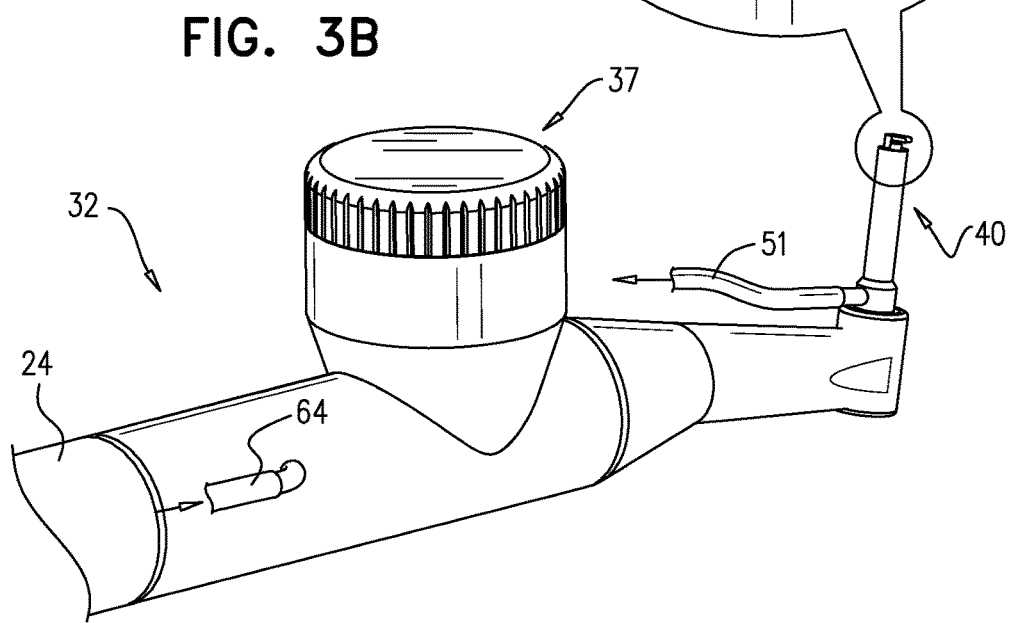
FIG. 3B

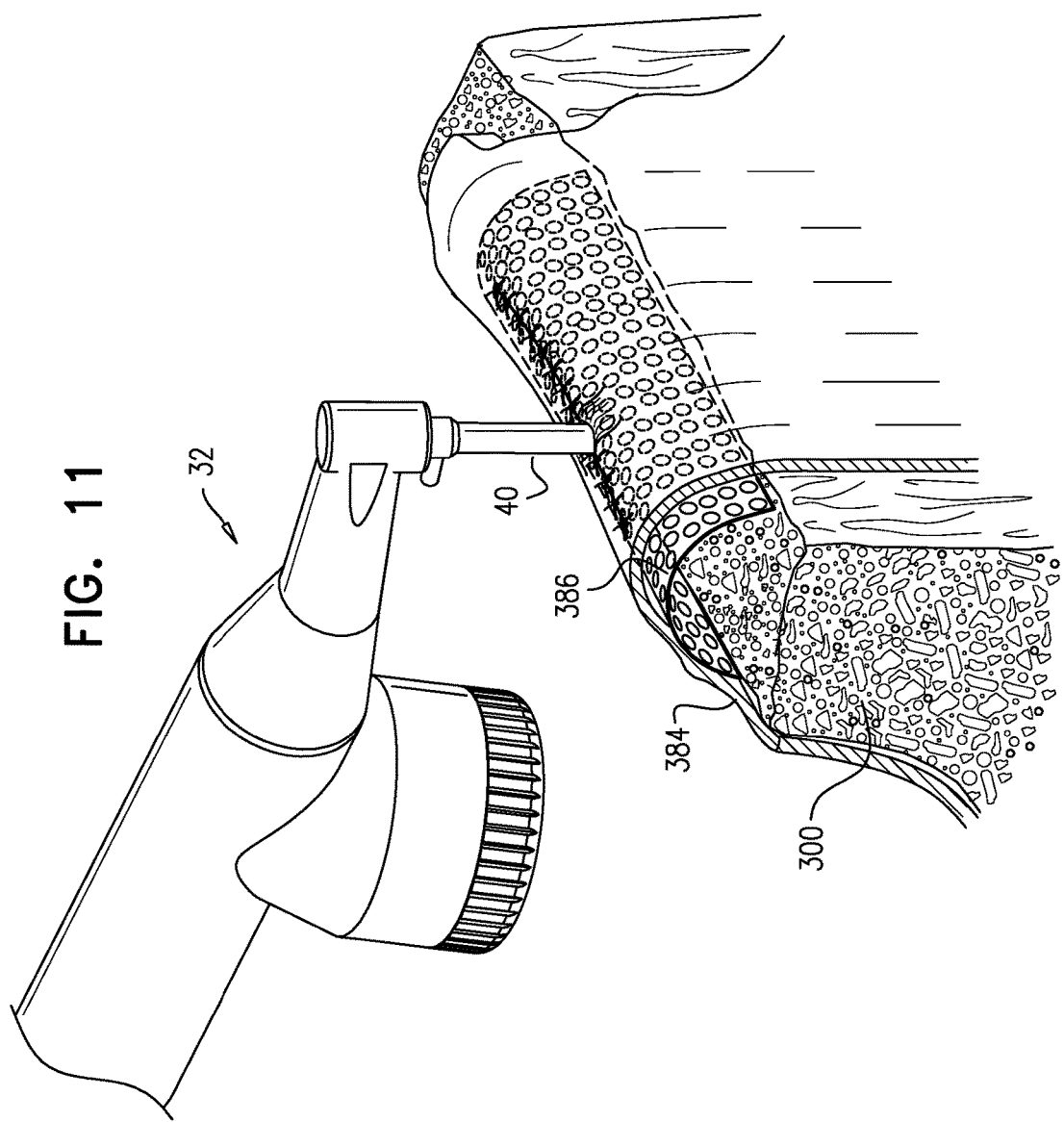

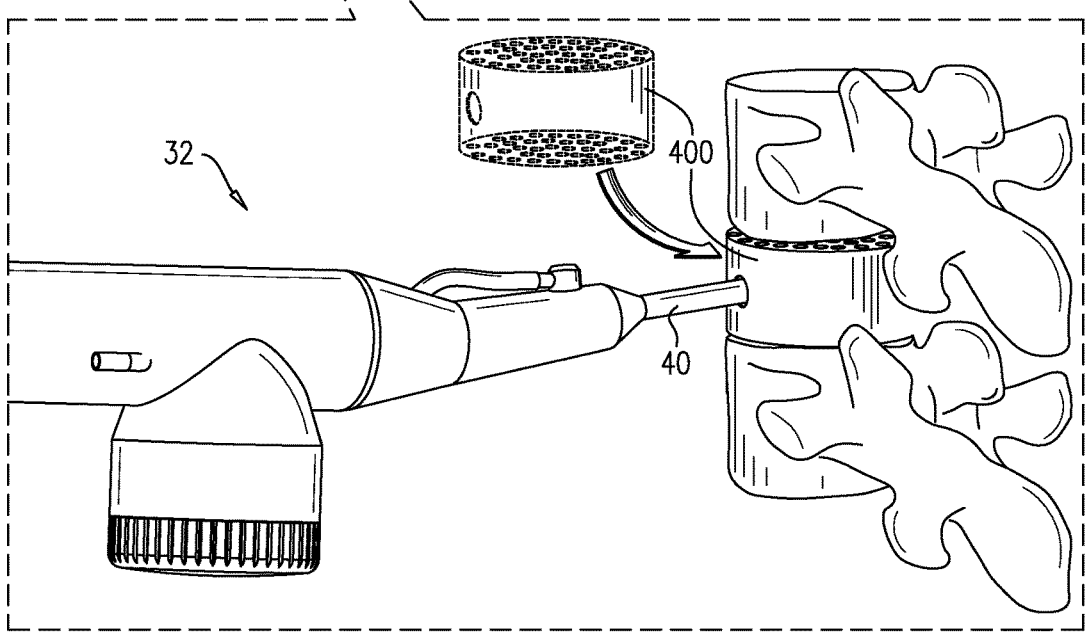
FIG. 12A
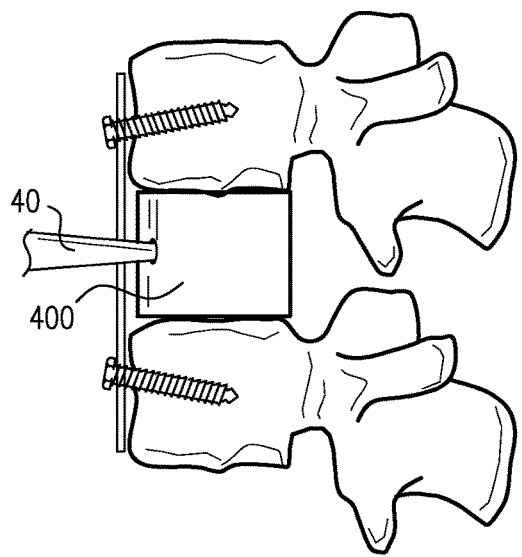
FIG. 12B

BONE GRAFT INJECTION METHODS

CROSS-REFERENCE TO RELATED APPLICATIONS

The present application claims the benefit of U.S. Provisional Application 62/150,969, filed Apr. 22, 2015, which is assigned to the assignee of the present application and is incorporated herein by reference.

FIELD OF THE APPLICATION

The present invention relates generally to surgical tools and implantation methods, and specifically to minimally-invasive surgical tools and implantation methods.

BACKGROUND OF THE APPLICATION

Osseointegrated dental implants are typically metallic or ceramic screws that are placed in the jawbone for supporting artificial teeth after the loss of natural teeth. Replacement of the maxillary teeth is often a challenging surgical procedure when the remaining maxillary bone has insufficient height to support the implant. One surgical technique for augmenting the maxillary bone includes injecting a regenerative material, such as autogenic, allogeneic, xenogeneic, or synthetic bone graft, into the vicinity of the maxillary bone. The regenerative material forms additional bone mass that integrates with the existing maxillary bone, providing the necessary alveolar height to support the implant.

Bone augmentation procedures are often surgically difficult to perform, and are associated with complications, including infection of the maxillary sinus. The top of the maxillary alveolar ridge forms the floor of the maxillary sinus, and is covered by a thin membrane known as the Schneiderian or subantral membrane. In one surgical procedure, known as a closed or internal sinus lift or elevation procedure, the surgeon drills a bore through the maxillary alveolar ridge from the oral cavity at the desired location of the implant. The bore penetrates the ridge to below the Schneiderian membrane. The surgeon injects the regenerative material through the bore to below the membrane, forming a cavity defined by the top of the ridge and the bottom of the membrane, which cavity occupies a portion of the space initially occupied by the maxillary sinus.

To prevent potentially serious complications, the surgeon must be careful not to perforate the Schneiderian membrane. This is often difficult, because of the delicacy of the membrane, and the restricted access afforded by the closed approach.

Hydraulic sinus lifting is performed by applying hydraulic pressure between the sinus floor and the Schneiderian membrane. The hydraulic elevation can be performed via a crestal or lateral approach. Once the membrane is elevated, using a hydraulic, closed, or lateral window technique, a bone graft material is applied, typically using one of two conventional techniques. The first conventional technique is the mechanical insertion of bone graft, which is formulated in small particles. This technique is manually demanding, and it may cause application of unequal stresses to the membrane, which may result in perforation of the membrane. The second conventional technique is the injection of bone graft in a gel formulation by applying the same principles of hydraulic elevation used during raising of the membrane.

SUMMARY

Some embodiments of the present invention provide a surgical tool for use in conjunction with minimally-invasive sinus lift techniques for augmenting the maxillary alveolar ridge while reducing the risk of perforating the Schneiderian membrane and of infection. The surgical tool is configured to inject, through a bore (osteotomy) and into a sinus cavity, a solid-liquid composition of bone graft particles and a physiological liquid solution, and to drain the physiological liquid solution through the same bore, leaving the bone graft particles in the cavity. Typically, a filter of the surgical tool is used to inhibit passage of bone graft particles from the cavity. Typically, hydraulic pressure is equally applied on the Schneiderian membrane by the solid-liquid composition throughout the injection of the solid-liquid composition. Such uniform hydraulic pressure prevents bone graft particles from applying local or uneven pressure on the Schneiderian membrane, and thus reduces the risk of perforation. The surgeon further screws an implant into the bone graft material in the cavity, either during the same procedure or after bone grows into the bone graft material. After bone grows into the bone graft material, a dental appliance, such as a crown, is coupled to the implant.

For some applications, the surgical tool comprises an automated device that both prepares (e.g., mixes) and delivers the solid-liquid composition during the procedure.

There is therefore provided, in accordance with an application of the present invention, apparatus including a surgical tool for use with solid particles and a physiological liquid solution, the surgical tool including:

exactly one shaft unit, which is shaped so as to define a delivery lumen and a drainage lumen;

a distal opening, which is disposed within 10 mm of a distal end of the shaft unit, in fluid communication with the delivery lumen;

a composition source, which is coupled in fluid communication with the delivery lumen, and which is configured to provide a solid-liquid composition of the solid particles and the physiological liquid solution; and a filter, which is disposed in fluid communication with the drainage lumen, and which is configured to inhibit passage of the solid particles of the solid-liquid composition and allow passage of the physiological liquid solution of the solid-liquid composition.

For some applications, the surgical tool is configured as an oral surgical tool. For some applications, the solid particles are bone graft particles, and the surgical tool is for use with the bone graft particles.

For some applications, the distal opening is disposed within 5 mm of the distal end of the shaft unit. For some applications, the distal opening is disposed at the distal end of the shaft unit.

For some applications, the distal opening includes a nozzle.

For some applications, the filter is disposed within 10 mm of the distal end of the shaft unit.

For some applications, the surgical tool is configured to vibrate the solid-liquid composition in the delivery lumen.

For some applications, the filter is disposed around an axis of the distal opening. For some applications, the drainage lumen is disposed around the delivery lumen in the shaft unit. For some applications, the drainage lumen is disposed alongside the delivery lumen in the shaft unit.

For some applications, the filter is disposed around the delivery lumen in the shaft unit.

For some applications, the surgical tool further includes a suction source, which is coupled in fluid communication with the drainage lumen. For some applications, the apparatus is for use with a suction source, and the drainage lumen is coupleable in fluid communication with the suction source.

For some applications, the apparatus further includes a pump, which is configured to clear the solid particles that accumulate on the filter during drainage of the physiological liquid solution through the filter, by periodically applying a positive pressure to the drainage lumen.

For some applications, the filter includes a mesh having openings smaller than the solid particles. For some applications, the filter is shaped so as to define a plurality of slits having a width narrower than the solid particles.

For some applications, the surgical tool further includes a sealing element disposed around an external surface of the shaft unit, and configured to form a liquid-tight seal with tissue around and outside a bore through a bone when the shaft unit is inserted into the bore. For some applications, the distal end of the shaft unit is disposed no more distal than a distal-most surface of the sealing element.

For some applications, the surgical tool further includes a depth limiting element, which is configured to limit a depth of insertion of the shaft unit into a bore through a bone when the shaft unit is inserted into the bore.

For some applications, the composition source includes a combining feeder unit, which is configured to provide the solid-liquid composition by combining the solid particles with the physiological liquid solution. For some applications, the combining feeder unit includes a mixing feeder unit, which is configured to provide the solid-liquid composition by mixing the solid particles with the physiological liquid solution. For some applications, the surgical tool is configured to move the distal opening and the shaft unit with respect to each other. For some applications, the distal opening includes a nozzle. For some applications, the surgical tool further includes a filter clearing element, which is fixed to the distal opening, and is configured to clear the solid particles that accumulate on the filter during drainage of the physiological liquid solution through the filter. For some applications, the distal opening includes a nozzle, and the filter clearing element is fixed to the nozzle.

For some applications, the surgical tool is configured to rotate the distal opening and the shaft unit with respect to each other. For some applications, the surgical tool is configured to rotate the distal opening while holding the shaft unit rotationally immobile. For some applications, the surgical tool is configured to rotate the shaft unit while holding the distal opening rotationally immobile.

For some applications, the surgical tool further includes a filter clearing element, which is fixed to the distal opening, and is configured to clear the solid particles that accumulate on the filter during drainage of the physiological liquid solution through the filter. For some applications, the surgical tool is configured to move the distal opening and the shaft unit side-to-side with respect to each other. For some applications, the surgical tool is configured to move the distal opening and the shaft unit axially back-and-forth with respect to each other. For some applications, the surgical tool is configured to vibrate the distal opening and the shaft unit side-to-side with respect to each other. For some applications, the surgical tool is configured such that flow of the solid-liquid composition causes the distal opening and the shaft unit to move with respect to each other. For some applications, the surgical tool is configured such that flow of the filtered physiological liquid solution causes the distal opening and the shaft unit to move with respect to each other. For some applications, the surgical tool is configured to automatically apply motion to the shaft unit selected from the group consisting of: vibrational motion, rotational motion, oscillatory motion, axial back-and-forth motion, and lateral side-to-side motion.

For some applications, the surgical tool further includes a filter clearing element, which is configured to clear the solid particles that accumulate on the filter during drainage of the physiological liquid solution through the filter. For some applications, the surgical tool is configured to move the filter clearing element with respect to the filter. For some applications, the surgical tool is configured to rotate the filter clearing element. For some applications, the surgical tool is configured to axially move the filter clearing element. For some applications, the filter clearing element is fixed to the distal opening. For some applications, the distal opening includes a nozzle, and the filter clearing element is fixed to the nozzle.

For some applications, the apparatus further includes a pump, which is configured to pump the solid-liquid composition through the distal opening via the delivery lumen. For some applications, the pump is configured to pump the solid-liquid composition at a pulsating positive hydraulic pressure. For some applications, the pump is configured to pump the solid-liquid composition at a pulsating hydraulic pressure that periodically varies between positive and negative.

For some applications, the surgical tool further includes a solid-particle container, which contains the solid particles for combining with the physiological liquid solution. For some applications, the solid-particle container has a volume of between 0.2 and 20 ml.

For some applications, the surgical tool further includes the physiological liquid solution.

There is further provided, in accordance with an application of the present invention, apparatus including a surgical tool for use with solid particles and a physiological liquid solution, the surgical tool including:

exactly one shaft unit, which is shaped so as to define a lumen;

a distal opening, which is disposed within 10 mm of a distal end of the shaft unit, in fluid communication with the lumen;

a composition source, which is coupled in selective fluid communication with the lumen, and which is configured to provide a solid-liquid composition of the solid particles and the physiological liquid solution; and a one-way filter, which is disposed in fluid communication with the lumen, and which is configured to:
  allow passage, in a proximal-to-distal direction, of the solid particles and the physiological liquid solution of the solid-liquid composition,
  inhibit passage, in a distal-to-proximal direction, of the solid particles of the solid-liquid composition, and
  allow passage, in the distal-to-proximal direction, of the physiological liquid solution of the solid-liquid composition.

For some applications, the surgical tool is configured as an oral surgical tool. For some applications, the solid particles are bone graft particles, and the surgical tool is for use with the bone graft particles.

For some applications, the distal opening is disposed within 5 mm of the distal end of the shaft unit. For some applications, the distal opening is disposed at the distal end of the shaft unit.

For some applications, the shaft unit is shaped so as to define exactly one lumen.

For some applications, the one-way filter is disposed within 10 mm of the distal end of the shaft unit.

For some applications, the composition source includes a combining feeder unit, which is configured to produce the solid-liquid composition by combining the solid particles with the physiological liquid solution.

For some applications, the distal opening includes a nozzle.

For some applications, the surgical tool is configured to automatically apply motion to the shaft unit selected from the group consisting of: vibrational motion, rotational motion, oscillatory motion, axial back-and-forth motion, and lateral side-to-side motion.

For some applications, the surgical tool is configured to vibrate the solid-liquid composition in the lumen.

For some applications, the surgical tool further includes a sealing element disposed around an external surface of the shaft unit, and configured to form a liquid-tight seal with tissue around and outside a bore through a bone when the shaft unit is inserted into the bore. For some applications, the distal end of the shaft unit is disposed no more distal than a distal-most surface of the sealing element.

For some applications, the surgical tool further includes a depth limiting element, which is configured to limit a depth of insertion of the shaft unit into a bore through a bone when the shaft unit is inserted into the bore.

For some applications, the apparatus further includes a one-way filter valve that includes the one-way filter, the one-way filter valve in fluid communication with the lumen. For some applications, the one-way filter valve includes a leaf valve, which includes one or more leafs that include mesh having openings smaller than the solid particles. For some applications, the one-way filter valve includes a leaf valve, which includes one or more leafs that are shaped so as to define a plurality of slits having a width narrower than the solid particles.

For some applications, the apparatus is for use with a suction source, and the surgical tool is shaped so as to define a suction port, and the one-way filter is in selective fluid communication with the suction source via the suction port. For some applications, the suction port is disposed at a site along a fluid path between the one-way filter and the composition source, and the surgical tool further includes a source one-way valve, which is disposed along the fluid path proximal to the site at which the suction port is disposed.

For some applications, the surgical tool is shaped so as to define a suction port, and the apparatus further includes a suction source, which is in selective fluid communication with the one-way filter via the suction port. For some applications, the suction port is disposed at a site along a fluid path between the one-way filter and the composition source, and the surgical tool further includes a source one-way valve, which is disposed along the fluid path proximal to the site at which the suction port is disposed.

For some applications, the surgical tool further includes a filter clearing element, which is configured to clear the solid particles that accumulate on the one-way filter during drainage of the physiological liquid solution through the one-way filter. For some applications, the surgical tool is configured to move the filter clearing element with respect to the one-way filter.

For some applications, the apparatus further includes a pump, which is configured to pump the solid-liquid composition through the distal opening via the lumen. For some applications, the pump is configured to pump the solid-liquid composition with an on-off duty cycle. For some applications, the apparatus is for use with a suction source, the surgical tool is shaped so as to define a suction port, the one-way filter is in selective fluid communication with the suction source via the suction port, and suction port is configured to assume an open state when the pump is off, and a closed state when the pump is on. For some applications, the surgical tool is shaped so as to define a suction port, and the apparatus further includes a suction source, which is in selective fluid communication with the one-way filter via the suction port, and which is configured to apply suction when the pump is off, and not apply the suction when the pump is on. For some applications, the pump is configured to pump the solid-liquid composition at a pulsating positive hydraulic pressure. For some applications, the pump is configured to pump the solid-liquid composition at a pulsating hydraulic pressure that periodically varies between positive and negative.

For some applications, the surgical tool further includes a solid-particle container, which contains the solid particles for mixing with the physiological liquid solution. For some applications, the solid-particle container has a volume of between 0.2 and 20 ml.

For some applications, the surgical tool further includes the physiological liquid solution.

There is still further provided, in accordance with an application of the present invention, apparatus including an osteotome, which is shaped so as to define:

a lumen through the osteotome, a distal end of the lumen opening through a distal opening disposed within 10 mm of a distal end of the osteotome, and a proximal end of the lumen opening through a proximal opening disposed at least 5 mm proximal to the distal opening, a lateral external surface, at least a portion of which is shaped so as to define a screw thread that (a) has a distal thread end that is disposed within 10 mm of the distal end of the osteotome, and (b) includes one or more raised helical ribs going around the osteotome, and one or more longitudinal drainage slots, which extend along at least respective longitudinal portions of the osteotome having respective longitudinal lengths of at least 5 mm, measured parallel to a central longitudinal axis of the osteotome.

For some applications, the osteotome is configured as a dental osteotome.

For some applications, the longitudinal lengths of the respective longitudinal portions are at least 8 mm, such as at least 10 mm, e.g., at least 12 mm.

For some applications, the proximal opening is disposed within 10 mm of a proximal end of the osteotome.

For some applications, at least one of the one or more longitudinal drainage slots reaches a proximal end of the osteotome.

For some applications, respective distal ends of the one or more longitudinal drainage slots are disposed at least one pitch of the screw thread from the distal thread end. For some applications, respective distal ends of the one or more longitudinal drainage slots are disposed at least two pitches of the screw thread from the distal thread end.

For some applications, the screw thread is multi-start.

For some applications, the osteotome further includes a sealing element disposed around an external surface of the osteotome, and configured to form a liquid-tight seal with tissue around and outside a bore through a bone when the osteotome is inserted into the bore.

For some applications, respective distal ends of the one or more longitudinal drainage slots are disposed at least 1.5 mm from the distal end of the osteotome. For some applications, respective distal ends of the one or more longitudinal drainage slots are disposed at least 4 mm from the distal end of the osteotome.

For some applications, the osteotome further includes a sealing element disposed around an external surface of the osteotome, and configured to form a liquid-tight seal with tissue around and outside a bore through a bone when the osteotome is inserted into the bore.

For some applications, respective average widths of the one or more longitudinal drainage slots are no more than 2 mm.

For some applications, respective average depths of the one or more longitudinal drainage slots, measured with respect to an outermost portion of the screw thread, are at least 10% greater than an average depth of the screw thread.

For some applications, the one or more longitudinal drainage slots cross the one or more ribs respective pluralities of times.

For some applications, the one or more longitudinal drainage slots include two or more longitudinal drainage slots.

For some applications, the one or more longitudinal drainage slots are parallel to the longitudinal axis.

For some applications, the one or more longitudinal drainage slots helically go around the osteotome in a direction opposite to a direction of the screw thread. For some applications, the one or more longitudinal drainage slots helically go around the osteotome with a slot pitch greater than a thread pitch of the screw thread.

For some applications, the slot pitch equals at least 1.5 times the thread pitch.

For some applications, the screw thread has one or more starts, and the slot pitch equals at least the quotient of (a) 2 mm divided by (b) the number of starts of the screw thread.

For some applications, the screw thread has one or more starts and a corresponding number of roots, and the osteotome is shaped so as to define a number of longitudinal drainage slots that corresponds to a number of the starts of the screw thread, and which are disposed within the one or more roots of the screw thread, respectively.

For some applications, a distal end of the one or more longitudinal drainage slots is disposed at least one pitch of the screw thread from the distal thread end.

For some applications, the distal end of the longitudinal drainage slot is disposed at least two pitches of the screw thread from the distal thread end.

For some applications, the osteotome further includes a sealing element disposed around an external surface of the osteotome, and configured to form a liquid-tight seal with tissue around and outside a bore through a bone when the osteotome is inserted into the bore.

For some applications, the apparatus is for use with solid particles and a physiological liquid solution, and the apparatus further including a composition source, which is coupled in fluid communication with the lumen, and which is configured to provide a solid-liquid composition of the solid particles and the physiological liquid solution. For some applications, the composition source includes a combining feeder unit, which is configured to provide the solid-liquid composition by combining the solid particles with the physiological liquid solution. For some applications, the combining feeder unit includes a mixing feeder unit, which is configured to provide the solid-liquid composition by mixing the solid particles with the physiological liquid solution.

There is additionally provided, in accordance with an application of the present invention, a method including:

inserting, from a first side of a bone, exactly one shaft unit of a surgical tool into a bore that passes through the bone from the first side to a second side of the bone, such that a distal opening disposed within 10 mm of a distal end of the shaft unit is disposed in the bore or in a cavity adjacent to the second side of the bone, wherein the distal opening is in fluid communication with a delivery lumen defined by the shaft unit;

providing a solid-liquid composition of solid particles and a physiological liquid solution from a composition source that is coupled in fluid communication with the delivery lumen; and injecting the solid-liquid composition through the delivery lumen and the distal opening into the cavity, such that (a) a portion of the physiological liquid solution drains through a filter of the surgical tool, and (b) the filter inhibits passage of solid particles of the solid-liquid composition such that the solid particles accumulate in the cavity, wherein the filter is disposed in fluid communication with a drainage lumen defined by the shaft unit.

For some applications, the surgical tool is configured as an oral surgical tool, the bone is a bone of a jaw, and inserting includes inserting the exactly one shaft unit of the oral surgical tool into the bore that passes through the bone of the jaw.

For some applications, the cavity is between the second side of the bone and a membrane. For some applications, the method further includes, before injecting the solid-liquid composition, raising the membrane to form the cavity between the second side of the bone and the membrane. For some applications, the membrane is a Schneiderian membrane.

For some applications, the bore is exactly one bore through the bone.

For some applications, the method further includes, after injecting the solid-liquid composition, implanting an implant at least partially within the cavity.

For some applications, the distal opening is disposed within 5 mm of the distal end of the shaft unit.

For some applications, the distal opening is disposed at the distal end of the shaft unit.

For some applications, injecting the solid-liquid composition includes injecting the solid-liquid composition such that at least 50% of the physiological liquid solution drains through the filter in a distal-to-proximal direction.

For some applications, injecting the solid-liquid composition includes injecting 2-300 ml of the solid-liquid composition.

For some applications, providing the solid-liquid composition and injecting the solid-liquid composition includes providing the solid-liquid composition and injecting the solid-liquid composition such that between 0.2 and 20 ml of solid particles accumulate in the cavity.

For some applications, injecting includes injecting the solid-liquid composition through the delivery lumen and the distal opening into the cavity, such that at least 50% of the physiological liquid solution drains through the filter while the solid-liquid composition is being injected.

For some applications, the composition source includes a combining feeder unit, and providing the solid-liquid composition includes activating the combining feeder unit to provide the solid-liquid composition by combining the solid particles with the physiological liquid solution. For some applications, the combining feeder unit includes a mixing feeder unit, and providing the solid-liquid composition includes activating the mixing feeder unit to provide the solid-liquid composition by mixing the solid particles with the physiological liquid solution.

For some applications, the filter is disposed within 10 mm of the distal end of the shaft unit.

There is yet additionally provided, in accordance with an application of the present invention, a method including:

placing a sealing element of a surgical tool against tissue around and outside a bore that passes through a bone from a first side to a second side of the bone, such that:

the sealing element forms a liquid-tight seal with the tissue on the first side of the bone, and a distal opening of the surgical tool is disposed in fluid communication with the bore, wherein the distal opening is in fluid communication with a delivery lumen defined by the surgical tool;

providing a solid-liquid composition of solid particles and a physiological liquid solution from a composition source that is coupled in fluid communication with the delivery lumen; and injecting the solid-liquid composition through the delivery lumen, the distal opening, and the bore, into a cavity adjacent to the second side of the bone, such that (a) a portion of the physiological liquid solution drains through a filter of the surgical tool, and (b) the filter inhibits passage of solid particles of the solid-liquid composition such that the solid particles accumulate in the cavity, wherein the filter is disposed in fluid communication with a drainage lumen defined by the surgical tool.

For some applications:

the sealing element disposed around an external surface of exactly one shaft unit of the surgical tool, the distal opening disposed within 10 mm of a distal end of the shaft unit, the delivery lumen is defined at least in part by the shaft unit, and the drainage lumen is defined at least in part by the shaft unit.

For some applications, the distal opening is disposed within 5 mm of the distal end of the shaft unit. For some applications, the distal opening is disposed at the distal end of the shaft unit.

For some applications, the filter is disposed within 10 mm of the distal end of the shaft unit.

For some applications, the surgical tool is configured as an oral surgical tool, the bone is a bone of a jaw, and placing includes placing the sealing element against the tissue around and outside the bore the passes through the bone of the jaw.

For some applications, the cavity is between the second side of the bone and a membrane.

For some applications, the method further includes, before injecting the solid-liquid composition, raising the membrane to form the cavity between the second side of the bone and the membrane. For some applications, the membrane is a Schneiderian membrane.

For some applications, the bore is exactly one bore through the bone.

For some applications, the method further includes, after injecting the solid-liquid composition, implanting an implant at least partially within the cavity.

For some applications, injecting the solid-liquid composition includes injecting the solid-liquid composition such that at least 50% of the physiological liquid solution drains through the filter in a distal-to-proximal direction.

For some applications, injecting the solid-liquid composition includes injecting 2-300 ml of the solid-liquid composition.

For some applications, providing the solid-liquid composition and injecting the solid-liquid composition includes providing the solid-liquid composition and injecting the solid-liquid composition such that between 0.2 and 20 ml of solid particles accumulate in the cavity.

For some applications, injecting includes injecting the solid-liquid composition through the delivery lumen and the distal opening into the cavity, such that at least 50% of the physiological liquid solution drains through the filter while the solid-liquid composition is being injected. For some applications, the composition source includes a combining feeder unit, and providing the solid-liquid composition includes activating the combining feeder unit to provide the solid-liquid composition by combining the solid particles with the physiological liquid solution. For some applications, the combining feeder unit includes a mixing feeder unit, and providing the solid-liquid composition includes activating the mixing feeder unit to provide the solid-liquid composition by mixing the solid particles with the physiological liquid solution.

There is also provided, in accordance with an application of the present invention, a method including:

inserting, from a first side of a bone, exactly one shaft unit of a surgical tool into a bore that passes through the bone from the first side to a second side of the bone, such that a distal opening disposed within 10 mm of a distal end of the shaft unit is disposed in the bore or in a cavity adjacent to the second side of the bone, wherein the distal opening is in fluid communication with a lumen defined by the shaft unit;

providing a solid-liquid composition of solid particles and a physiological liquid solution from a composition source that is coupled in fluid communication with the lumen; and injecting the solid-liquid composition through the lumen, a one-way filter of the surgical tool, and the distal opening into the cavity, the one-way filter disposed in fluid communication with the lumen, and configured to:

allow passage, in a proximal-to-distal direction, of the solid particles and the physiological liquid solution of the solid-liquid composition, inhibit passage, in a distal-to-proximal direction, of the solid particles of the solid-liquid composition, such that the solid particles accumulate in the cavity, and allow passage, in the distal-to-proximal direction, of the physiological liquid solution of the solid-liquid composition.

For some applications, the surgical tool is configured as an oral surgical tool, the bone is a bone of a jaw, and inserting includes inserting the exactly one shaft unit of the oral surgical tool into the bore that passes through the bone of the jaw.

For some applications, the cavity is between the second side of the bone and a membrane. For some applications, the method further includes, before injecting the solid-liquid composition, raising the membrane to form the cavity between the second side of the bone and the membrane. For some applications, the membrane is a Schneiderian membrane.

For some applications, the bore is exactly one bore through the bone.

For some applications, the method further includes, after injecting the solid-liquid composition, implanting an implant at least partially within the cavity.

For some applications, the distal opening is disposed within 5 mm of the distal end of the shaft unit.

For some applications, the distal opening is disposed at the distal end of the shaft unit.

For some applications, the method further includes draining the physiological liquid solution of the solid-liquid composition through the one-way filter. For some applications, injecting and draining include alternatingly injecting and draining.

For some applications, injecting the solid-liquid composition includes pumping the solid-liquid composition at a positive hydraulic pressure, and draining the physiological liquid solution includes suctioning the physiological liquid solution at a negative hydraulic pressure.

For some applications, pumping and suctioning include alternatingly pumping and suctioning.

For some applications, injecting the solid-liquid composition includes injecting the solid-liquid composition such that at least 50% of the physiological liquid solution drains through the one-way filter in the distal-to-proximal direction.

For some applications, injecting the solid-liquid composition includes injecting 2-300 ml of the solid-liquid composition.

For some applications, providing the solid-liquid composition and injecting the solid-liquid composition includes providing the solid-liquid composition and injecting the solid-liquid composition such that between 0.2 and 20 ml of solid particles accumulate in the cavity.

For some applications, the composition source includes a combining feeder unit, and providing the solid-liquid composition includes activating the combining feeder unit to provide the solid-liquid composition by combining the solid particles with the physiological liquid solution. For some applications, the combining feeder unit includes a mixing feeder unit, and providing the solid-liquid composition includes activating the mixing feeder unit to provide the solid-liquid composition by mixing the solid particles with the physiological liquid solution.

For some applications, the one-way filter is disposed within 10 mm of the distal end of the shaft unit.

There is further provided, in accordance with an application of the present invention, a method including:

placing a sealing element of a surgical tool against tissue around and outside a bore that passes through a bone from a first side to a second side of the bone, such that:
  the sealing element forms a liquid-tight seal with the tissue on the first side of the bone, and
  a distal opening of the surgical tool is disposed in fluid communication with the bore, wherein the distal opening is in fluid communication with a lumen defined by the surgical tool;

providing a solid-liquid composition of solid particles and a physiological liquid solution from a composition source that is coupled in fluid communication with the lumen; and injecting the solid-liquid composition through the lumen, a one-way filter of the surgical tool, the distal opening, and the bore, into a cavity adjacent to the second side of the bone, wherein the one-way filter is disposed in fluid communication with the lumen, and configured to:
  allow passage, in a proximal-to-distal direction, of the solid particles and the physiological liquid solution of the solid-liquid composition,
  inhibit passage, in a distal-to-proximal direction, of the solid particles of the solid-liquid composition, such that the solid particles accumulate in the cavity, and
  allow passage, in the distal-to-proximal direction, of the physiological liquid solution of the solid-liquid composition.

For some applications:
the sealing element disposed around an external surface of exactly one shaft unit of the surgical tool,
the distal opening disposed within 10 mm of a distal end of the shaft unit, and
the lumen is defined at least in part by the shaft unit.

For some applications, the distal opening is disposed within 5 mm of the distal end of the shaft unit. For some applications, the distal opening is disposed at the distal end of the shaft unit.

For some applications, the one-way filter is disposed within 10 mm of the distal end of the shaft unit.

For some applications, the surgical tool is configured as an oral surgical tool, the bone is a bone of a jaw, and placing includes placing the sealing element against the tissue around and outside the bore that passes through the bone of the jaw.

For some applications, the cavity is between the second side of the bone and a membrane. For some applications, the method further includes, before injecting the solid-liquid composition, raising the membrane to form the cavity between the second side of the bone and the membrane. For some applications, the membrane is a Schneiderian membrane.

For some applications, the bore is exactly one bore through the bone.

For some applications, the method further includes, after injecting the solid-liquid composition, implanting an implant at least partially within the cavity.

For some applications, the method further includes draining the physiological liquid solution of the solid-liquid composition through the one-way filter. For some applications, injecting and draining include alternatingly injecting and draining.

For some applications, injecting the solid-liquid composition includes pumping the solid-liquid composition at a positive hydraulic pressure, and draining the physiological liquid solution includes suctioning the physiological liquid solution at a negative hydraulic pressure.

For some applications, pumping and suctioning include alternatingly pumping and suctioning.

For some applications, injecting the solid-liquid composition includes injecting the solid-liquid composition such that at least 50% of the physiological liquid solution drains through the one-way filter in the distal-to-proximal direction.

For some applications, injecting the solid-liquid composition includes injecting 2-300 ml of the solid-liquid composition.

For some applications, providing the solid-liquid composition and injecting the solid-liquid composition includes providing the solid-liquid composition and injecting the solid-liquid composition such that between 0.2 and 20 ml of solid particles accumulate in the cavity.

For some applications, the composition source includes a combining feeder unit, and providing the solid-liquid composition includes activating the combining feeder unit to provide the solid-liquid composition by combining the solid particles with the physiological liquid solution. For some applications, the combining feeder unit includes a mixing feeder unit, and providing the solid-liquid composition includes activating the mixing feeder unit to provide the solid-liquid composition by mixing the solid particles with the physiological liquid solution.

There is still further provided, in accordance with an application of the present invention, a method including:

injecting, from a first side of a bone, through (a) a bore that passes through the bone from the first side to a second side of the bone, and (b) into a cavity adjacent to the second side of the bone, a solid-liquid composition of solid particles and a physiological liquid solution; and draining, from the cavity and through the bore, the physiological liquid solution of the solid-liquid composition, while inhibiting passage of the solid particles of the solid-liquid composition, such that the solid particles accumulate in the cavity.

For some applications, inhibiting the passage of the solid particles includes using a filter to inhibit the passage of the solid particles.

For some applications, injecting the solid-liquid composition includes injecting the solid-liquid composition such that at least 50% of the physiological liquid solution drains through the filter in a distal-to-proximal direction.

For some applications, injecting the solid-liquid composition includes injecting 2-300 ml of the solid-liquid composition.

For some applications, the cavity is between the second side of the bone and a membrane. For some applications, the method further includes, before injecting the solid-liquid composition, raising the membrane to form the cavity between the second side of the bone and the membrane. For some applications, the membrane is a Schneiderian membrane.

For some applications, the bore is exactly one bore through the bone.

For some applications, the method further includes, after injecting the solid-liquid composition, implanting an implant at least partially within the cavity.

There is additionally provided, in accordance with an application of the present invention, a method including:

providing an osteotome, which is shaped so as to define (i) a lumen through the osteotome, a distal end of the lumen opening through a distal opening disposed within 10 mm of a distal end of the osteotome, and a proximal end of the lumen opening through a proximal opening disposed at least 5 mm proximal to the distal opening, (ii) a lateral external surface, at least a portion of which is shaped so as to define a screw thread that (a) has a distal thread end that is disposed within 10 mm of the distal end of the osteotome, and (b) includes one or more raised helical ribs going around the osteotome, and (iii) one or more longitudinal drainage slots, which extend along at least respective longitudinal portions of the osteotome having respective longitudinal lengths of at least 5 mm, measured parallel to a central longitudinal axis of the osteotome;

inserting, from a first side of a bone, the osteotome into a bore that passes through the bone from the first side to a second side of the bone, such that the distal opening is disposed in the bore or in a cavity adjacent to the second side of the bone;

providing a solid-liquid composition of solid particles and a physiological liquid solution from a composition source that is coupled in fluid communication with the lumen; and injecting the solid-liquid composition through the lumen and the distal opening into the cavity, such that (a) a portion of the physiological liquid solution drains through the one or more longitudinal drainage slots, and (b) the one or more longitudinal drainage slots inhibit passage of solid particles of the solid-liquid composition such that the solid particles accumulate in the cavity.

For some applications, the osteotome is configured as a dental osteotome, the bone is a bone of a jaw, and inserting includes inserting the dental osteotome into the bore that passes through the bone of the jaw.

For some applications, the cavity is between the second side of the bone and a membrane. For some applications, the method further includes, before injecting the solid-liquid composition, raising the membrane to form the cavity between the second side of the bone and the membrane.

For some applications:
respective distal ends of the one or more longitudinal drainage slots are disposed at least one pitch of the screw thread from the distal thread end,
raising the membrane includes:
advancing the osteotome into the bore such that a portion of the screw thread distal to the respective distal ends of the one or more longitudinal drainage slots sealingly engages a wall of the bore; and
thereafter, injecting a fluid through the bore under sufficient pressure to raise the membrane, and
the method further includes, before injecting the solid-liquid composition, further advancing the osteotome into the bore until the one or more drainage slots come into fluid communication with the cavity.

For some applications, the membrane is a Schneiderian membrane.

For some applications, the bore is exactly one bore through the bone.

For some applications, the method further includes, after injecting the solid-liquid composition, implanting an implant at least partially within the cavity.

For some applications, the longitudinal lengths of the respective longitudinal portions are at least 8 mm, such as at least 10 mm, e.g., at least 12 mm.

For some applications, the longitudinal lengths of the respective longitudinal portions are at least 2 mm greater than a thickness of the bone adjacently surrounding the bore.

For some applications, the proximal opening is disposed within 10 mm of a proximal end of the osteotome.

For some applications, at least one of the one or more longitudinal drainage slots reaches a proximal end of the osteotome.

For some applications, respective distal ends of the one or more longitudinal drainage slots are disposed at least one pitch of the screw thread from the distal thread end. For some applications, respective distal ends of the one or more longitudinal drainage slots are disposed at least two pitches of the screw thread from the distal thread end.

For some applications, the screw thread is multi-start.

For some applications, the osteotome further includes a sealing element disposed around an external surface of the osteotome, and inserting includes inserting the osteotome into the bore such that the sealing element forms a liquid-tight seal with tissue around and outside the bore.

For some applications, respective distal ends of the one or more longitudinal drainage slots are disposed at least 1.5 mm from the distal end of the osteotome. For some applications, respective distal ends of the one or more longitudinal drainage slots are disposed at least 4 mm from the distal end of the osteotome.

For some applications, the osteotome further includes a sealing element disposed around an external surface of the osteotome, and inserting includes inserting the osteotome into the bore such that the sealing element forms a liquid-tight seal with tissue around and outside the bore.

For some applications, respective average widths of the one or more longitudinal drainage slots are no more than 2 mm.

For some applications, respective average depths of the one or more longitudinal drainage slots, measured with respect to an outermost portion of the screw thread, are at least 10% greater than an average depth of the screw thread.

For some applications, the one or more longitudinal drainage slots cross the one or more ribs respective pluralities of times.

For some applications, the one or more longitudinal drainage slots include two or more longitudinal drainage slots.

For some applications, the one or more longitudinal drainage slots are parallel to the longitudinal axis.

For some applications, the one or more longitudinal drainage slots helically go around the osteotome in a direction opposite to a direction of the screw thread. For some applications, the one or more longitudinal drainage slots helically go around the osteotome with a slot pitch greater than a thread pitch of the screw thread.

For some applications, the slot pitch equals at least 1.5 times the thread pitch.

For some applications, the screw thread has one or more starts, and the slot pitch equals at least the quotient of (a) 2 mm divided by (b) the number of starts of the screw thread.

For some applications, the screw thread has one or more starts and a corresponding number of roots, and the osteotome is shaped so as to define a number of longitudinal drainage slots that corresponds to a number of the starts of the screw thread, and which are disposed within the one or more roots of the screw thread, respectively.

For some applications, a distal end of the one or more longitudinal drainage slots is disposed at least one pitch of the screw thread from the distal thread end.

For some applications, the distal end of the longitudinal drainage slot is disposed at least two pitches of the screw thread from the distal thread end.

For some applications, the osteotome further includes a sealing element disposed around an external surface of the osteotome, and inserting includes inserting the osteotome into the bore such that the sealing element forms a liquid-tight seal with tissue around and outside the bore.

For some applications, the method is for use with solid particles and a physiological liquid solution, and the method further includes providing a solid-liquid composition of the solid particles and the physiological liquid solution. For some applications, the composition source includes a combining feeder unit, and providing the solid-liquid composition includes activating the combining feeder unit to provide the solid-liquid composition by combining the solid particles with the physiological liquid solution. For some applications, the combining feeder unit includes a mixing feeder unit, and providing the solid-liquid composition includes activating the mixing feeder unit to provide the solid-liquid composition by mixing the solid particles with the physiological liquid solution.

The present invention will be more fully understood from the following detailed description of embodiments thereof, taken together with the drawings, in which:

BRIEF DESCRIPTION OF THE DRAWINGS

FIGS. 3A-B are schematic illustrations of respective configurations of the injector unit of FIG. 1, in accordance with respective applications of the present invention;

FIG. 11 is a schematic illustration of one use of the surgical tool of FIGS. 1-5B for ridge augmentation, in accordance with an application of the present invention;

FIGS. 12A-B are schematic illustrations of one use of the surgical tool of FIGS. 1-5B for performing a minimally-invasive spinal interbody fusion, in accordance with an application of the present invention.

DETAILED DESCRIPTION OF APPLICATIONS

Figure 1:
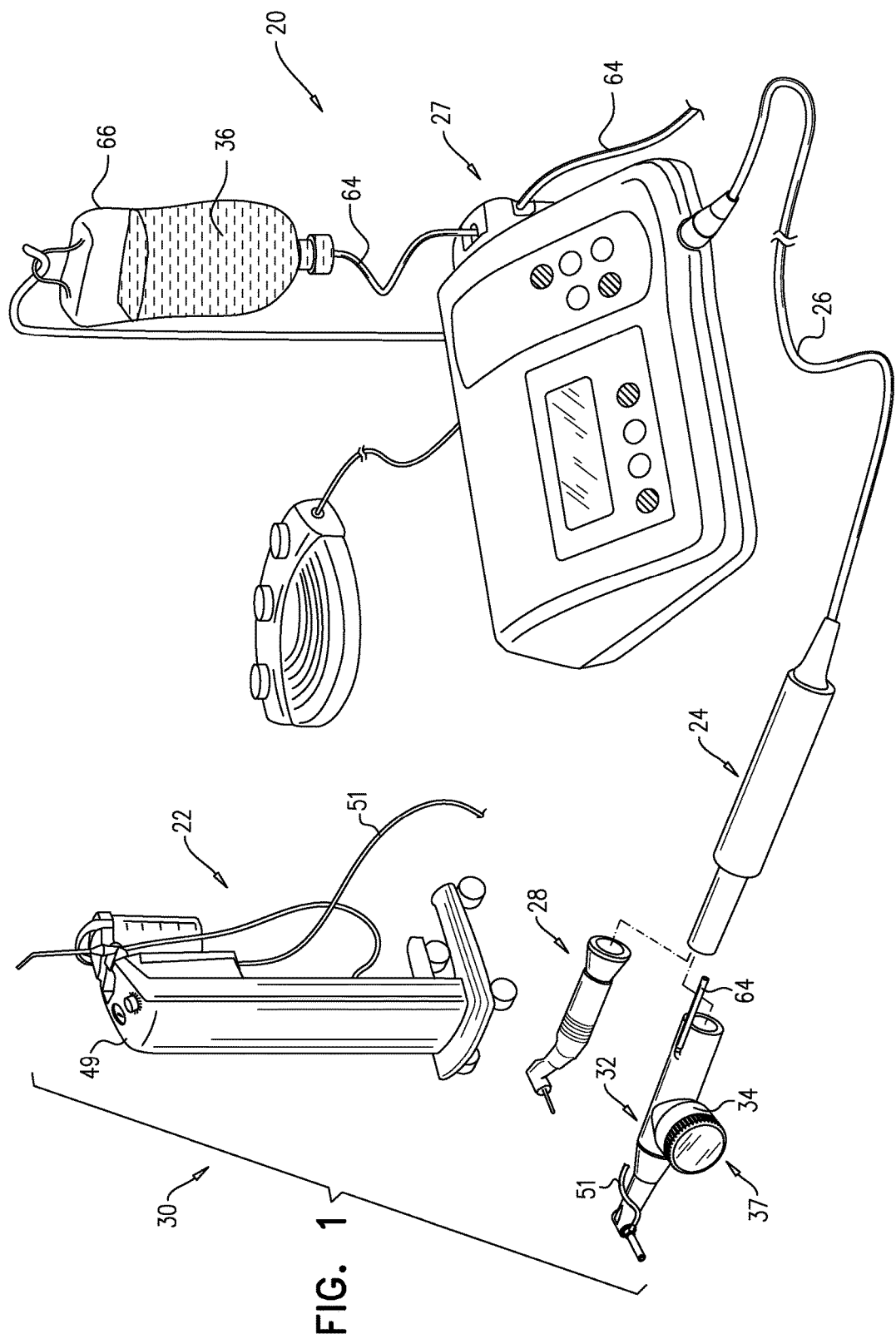
FIG. 1 is a schematic illustration of a surgical tool for the insertion of bone graft particles into a cavity, in accordance with an application of the present invention.

FIG. 1 is a schematic illustration of a surgical tool 20 for the insertion of bone graft particles into a cavity, in accordance with an application of the present invention. For some applications, surgical tool 20 is configured as an oral surgical tool. Surgical tool 20 may comprise one or more of the following components:

- a handheld motor 24, as is known in the art, which is typically connected to external control unit 22 by a cord 26;
- an external control unit 22, which optionally comprises a conventional surgical implant external control unit; typically, external control unit 22 comprises a power supply, electronics, and a user interface for controlling handheld motor 24, as is known in the art; for some application, external control unit 22 comprises a pump 27, such as a peristaltic pump, as is known in the art;
- one or more conventional drilling handpieces 28; and/or
- a foot control 30 for controlling external control unit 22, as is known in the art.

Figure 2A:
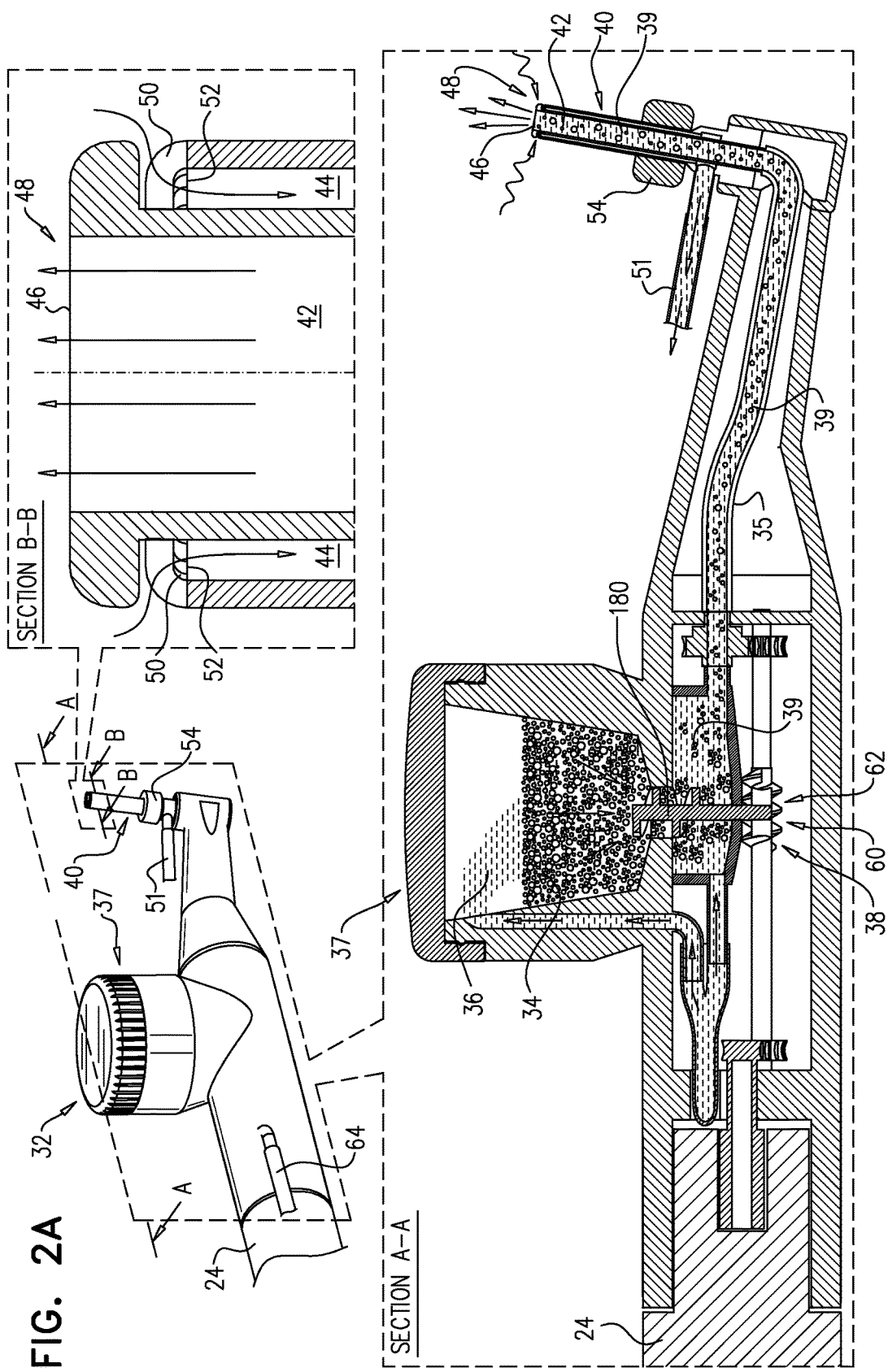
FIGS. 2A-B are schematic illustrations of respective configurations of an injector unit of the surgical tool of FIG. 1, in accordance with respective applications of the present invention.

Surgical tool 20 further comprises a handheld bone graft injector unit 32. For some applications, injector unit 32 is implemented as an attachment to a separate handheld motor 24, such as shown in FIGS. 1 and 2A. This implementation may allow a surgeon to leverage conventional equipment already available. For other applications, injector unit 32 is implemented as a standalone unit comprising its own motor, such as described hereinbelow with reference to FIG. 2B.

Surgical tool 20 is configured to be used with bone graft particles 34 and a physiological liquid solution 36, such as saline solution or blood. For some applications, the bone graft particles comprise natural bone mineral particles (either xenograft or allograft), synthetic particles, demineralized bone matrix, an autograft, or bioactive composites. To this end, surgical tool 20 comprises a composition source 38, which is configured to provide a solid-liquid composition 39 (labeled in FIGS. 2A-B) of bone graft particles 34 and physiological liquid solution 36. For some applications, physiological liquid solution 36 is substantially non-viscous, e.g., has a viscosity of water. Alternatively, physiological liquid solution 36 is somewhat viscous, e.g., may comprise glycerol or hyaluronic acid, which is sufficiently non-viscous to be injected and to drain under clinically-safe pressures. For some applications, solid-liquid composition 39 further comprises a radiopaque agent, to enable X-ray visualization of the procedure. For some applications, bone graft particles 34 have an average particle size (measured as the greatest dimension of each particle) of at least 0.01 mm, no more than 3 mm, and/or between 0.01 mm and 3 mm. For some applications, bone graft particles 34 comprise bone graft blocks, in which case the greatest dimension is selected for ready passage through delivery lumen 42, described hereinbelow. For some applications, composition source 38 comprises a combining feeder unit 60, such as described hereinbelow with reference to FIGS. 2A-B. For other applications, composition source 38 comprises a container of pre-combined bone graft particles 34 and physiological liquid solution 36; for example, the container may comprise a syringe. For some applications, injector unit 32 comprises composition source 38, while for other applications, composition source 38 is provided as a separate unit, e.g., a tabletop unit, or as a component of external control unit 22.

For some applications, surgical tool 20 (e.g., injector unit 32 thereof) further comprises a solid-particle container 37, which contains bone graft particles 34 for combining with physiological liquid solution 36. For example, solid-particle container 37 may have a volume of at least 0.2 ml, no more than 20 ml, and/or between 0.2 and 20 ml. Optionally, solid-particle container 37, in addition to bone graft particles 34, contains some physiological liquid solution 36, which may enable combining of bone graft particles 34 and physiological liquid solution 36 in solid-particle container 37, such as described hereinbelow with reference to FIGS. 8A-K.

For some applications, external control unit 22 is configured to display one or more of the following: (a) bone graft volume injected, (b) bone graft volume remaining, (c) pressure of solid-liquid composition 39, and/or (d) total volume injected (bone graft plus physiological liquid solution).

Figure 2B:
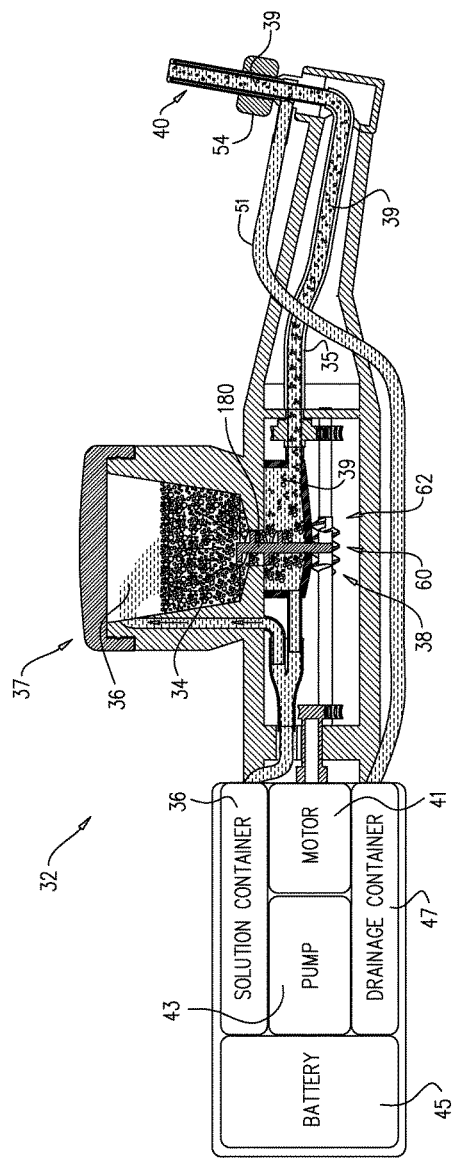

Reference is now made to FIGS. 2A-B, which are schematic illustrations of respective configurations of injector unit 32, in accordance with respective applications of the present invention.

In the configuration shown in FIG. 2A, injector unit 32 is implemented as an attachment to separate handheld motor 24.

In the configuration shown in FIG. 2B, injector unit 32 is implemented as a standalone unit, which typically comprises one or more of the following elements: (a) its own motor 41, (b) a pump 43, such as described hereinbelow, (c) a rechargeable or disposable battery 45, (d) liquid solution container 66, and/or (e) a drainage container 47. For some applications, injector unit 32 comprises a combined liquid-solution-drainage container instead of a separate liquid solution container 66 and a separate drainage container 47. This configuration provides close loop circulation of physiological liquid solution 36, and thus may, for example, allow the use of less physiological liquid solution 36 because the solution is reused during operation.

Injector unit 32 comprises exactly one shaft unit 40, which is shaped so as to define a delivery lumen 42 and a drainage lumen 44. Shaft unit 40 comprises one or more shafts, which may be arranged concentrically and/or alongside one another. Composition source 38 is coupled in fluid communication with delivery lumen 42, such as via a feeder tube 35, which optionally is flexible and/or transmits torque. Delivery lumen 42 and drainage lumen 44 are typically not in fluid communication with each other within shaft unit 40. Typically, a largest circle circumscribed by a cross-section of delivery lumen 42 has a diameter of at least 1 mm, such as at least 1.5 mm, and/or no more than 7 mm, such as no more than 4 mm (the cross-section is perpendicular to a longitudinal axis of the delivery lumen).

Injector unit 32 further comprises a distal opening 46, which is typically disposed within 10 mm of a distal end 48 of shaft unit 40 (e.g., within 5 mm of the distal end, such as at the distal end), in fluid communication with delivery lumen 42. For some applications, distal opening 46 comprises a nozzle, for controlling the direction and/or flow rate of the distribution of solid-liquid composition 39. The nozzle may be shaped so as to define one or more lateral or distal openings. As used in the present application, including in the claims, distal end 48 of shaft unit 40 means the distal-most point(s) of the shaft unit.

Injector unit 32 further comprises a filter 50, which is disposed in fluid communication with drainage lumen 44, and which is configured to (a) inhibit passage of bone graft particles 34 of solid-liquid composition 39 and (b) allow passage of physiological liquid solution 36 of solid-liquid composition 39. For some applications, filter 50 is disposed within 10 mm of distal end 48 of shaft unit 40, e.g., at distal end 48. For other applications filter 50 is disposed elsewhere along shaft unit 40, or outside of shaft unit 40 in fluid communication with drainage lumen 44. For some applications, such as shown in FIGS. 2A, 3A, and 3B, filter 50 is shaped so as to define a plurality of slits 52 having a width narrower than bone graft particles 34. Alternatively or additionally, for some applications, filter 50 comprises a mesh having openings smaller than bone graft particles 34.

For some applications, filter 50, distal opening 46, and/or solid-particle container 37 are detachable from surgical tool 20 and/or disposable.

As mentioned above, for some applications, composition source 38 comprises combining feeder unit 60, which is configured to provide solid-liquid composition 39 by combining bone graft particles 34 with physiological liquid solution 36. For some applications, combining feeder unit 60 comprises a mixing feeder unit 62, which is configured to provide solid-liquid composition 39 by mixing bone graft particles 34 with physiological liquid solution 36. Several possible configurations of mixing feeder unit 62 are described hereinbelow with reference to FIGS. 8A-K.

As described hereinbelow with reference to FIGS. 4 and 5A-B, injector unit 32 is configured to inject solid-liquid composition 39 through delivery lumen 42 and distal opening 46 into a cavity, such that (a) a portion of physiological liquid solution 36 drains through filter 50, and (b) filter 50 inhibits passage of bone graft particles 34 of solid-liquid composition 39, such that bone graft particles 34 accumulate in the cavity.

To enable such injection, for some applications surgical tool 20 further comprises a pump, which is configured to pump solid-liquid composition 39 through distal opening 46 via delivery lumen 42. For some applications, such as those in which injector unit 32 is implemented as an attachment to separate handheld motor 24 (such as shown in FIG. 2A), the pump comprises pump 27 of external control unit 22. In these applications, a supply tube 64 typically is coupled in fluid communication with (a) a liquid solution container 66 (such as a bag) that contains physiological liquid solution 36, and (b) combining feeder unit 60; supply tube 64 passes through pump 27. For other applications, such as those in which injector unit 32 is implemented as a standalone unit (such as shown in FIG. 2B), the pump comprises pump 43 of injector unit 32.

For some applications, the pump is configured to pump solid-liquid composition 39 at a pulsating positive hydraulic pressure. Such pulsation may help distribute solid-liquid composition 39 in the cavity, and/or inhibit clogging of filter 50, such as described hereinbelow. For some applications, the pump is configured to pump solid-liquid composition 39 at a pulsating hydraulic pressure that periodically varies between positive and negative (optionally, the negative pressure is applied a smaller portion of the time than is the positive pressure). Such pulsation may help inhibit clogging of filter 50, such as described hereinbelow.

For some applications, surgical tool 20 further comprises a suction source 49 (labeled in FIG. 1), which is coupled in fluid communication with drainage lumen 44, such as by a suction tube 51. The suction provided by suction source 49 facilitates drainage of the filtered physiological liquid solution 36. Alternatively, suction is not used, and passive drainage is sufficient, such as because of pressure build-up in the cavity generated by the injection of solid-liquid composition 39. For some applications, the pump is configured to clear bone graft particles 34 that accumulate on filter 50 during drainage of physiological liquid solution 36 through filter 50, by periodically applying a positive pressure to drainage lumen 44.

For some applications, surgical tool 20 (e.g., injector unit 32 thereof, such as shaft unit 40) is configured to inhibit clogging of filter 50 by bone graft particles 34 as physiological liquid solution 36 drains through filter 50. For some applications, surgical tool 20 (e.g., injector unit 32 thereof, such as shaft unit 40) is configured to move distal opening 46 and shaft unit 40 with respect to each other (for applications in which distal opening 46 comprises the nozzle, the nozzle and shaft unit 40 with respect to each other), for example during delivery of solid-liquid composition 39. For example, surgical tool 20 (e.g., injector unit 32 thereof, such as shaft unit 40) may be configured to:

rotate distal opening 46 and shaft unit 40 with respect to each other; the rotation may be either full or partial, and/or unidirectional and/or bidirectional; for some applications, surgical tool 20 (e.g., injector unit 32 thereof) is configured to rotate distal opening 46 while holding shaft unit 40 rotationally immobile, while for other applications, surgical tool 20 (e.g., injector unit 32 thereof) is configured to rotate shaft unit 40 while holding distal opening 46 rotationally immobile;

move distal opening 46 and shaft unit 40 side-to-side with respect to each other;

move distal opening 46 and shaft unit 40 axially back-and-forth with respect to each other; and/or vibrate distal opening 46 and shaft unit 40 side-to-side with respect to each other; and/or Alternatively or additionally, for some applications, surgical tool 20 (e.g., injector unit 32 thereof) is configured to automatically apply motion to shaft unit 40 selected from the group consisting of: vibrational motion, rotational motion, oscillatory motion, axial back-and-forth motion, and lateral side-to-side motion. Further alternatively or additionally, for some applications, surgical tool 20 (e.g., injector unit 32 thereof) is configured to vibrate solid-liquid composition 39 in delivery lumen 42.

For some applications, in order to provide any of the above-mentioned motions, surgical tool 20 uses electromagnetic power or pneumatic power.

For some applications, surgical tool 20 (e.g., injector unit 32 thereof, such as shaft unit 40) is configured such that flow of solid-liquid composition 39 causes distal opening 46 and shaft unit 40 to move with respect to each other. Alternatively or additionally, for some applications, surgical tool 20 (e.g., injector unit 32 thereof, such as shaft unit 40) is configured such that flow of filtered physiological liquid solution 36 causes distal opening 46 and shaft unit 40 to move with respect to each other.

For some applications, such as shown in FIG. 2A, surgical tool 20 (e.g., injector unit 32 thereof) further comprises a sealing element 54 disposed around an external surface of shaft unit 40, and configured to form a liquid-tight seal with tissue (gingiva or bone) around and outside a bore through the bone when shaft unit 40 is inserted into the bore. Sealing element 54 may inhibit flow of the filtered physiological liquid solution 36 into the patient's mouth. For some applications, surgical tool 20 (e.g., injector unit 32 thereof) further comprises a depth limiting element, which is configured to limit a depth of insertion of shaft unit 40 into a bore through a bone when shaft unit 40 is inserted into the bore. For some applications, element 54 alternatively or additionally serves as the depth limiting element.

Reference is now made to FIGS. 3A-B, which are schematic illustrations of respective configurations of injector unit 32, in accordance with respective applications of the present invention. In these configurations, surgical tool 20 (e.g., injector unit 32 thereof, such as shaft unit 40) further comprises a filter clearing element 70, which is configured to clear bone graft particles 34 that accumulate on filter 50 during drainage of physiological liquid solution 36 through filter 50. Filter clearing element 70 may also serve to distribute solid-liquid composition, in order to provide better distribution of bone graft particles 34 in cavity 90 and to prevent the bone graft particles from clogging distal opening 46.

For some applications, surgical tool 20 (e.g., injector unit 32 thereof) is configured to move filter clearing element 70 with respect to filter 50. For example, surgical tool 20 (e.g., injector unit 32 thereof) may be configured to (a) rotate filter clearing element 70 (the rotation may be either full or partial, and/or unidirectional and/or bidirectional); and/or (b) axially move filter clearing element 70.

For some applications, such as shown in FIGS. 3A-B, filter clearing element 70 is fixed to distal opening 46 (i.e., to the structure that defines distal opening 46). For some applications in which distal opening 46 comprises the nozzle, filter clearing element 70 is fixed to the nozzle. In some of these applications, the various motions of distal opening 46 and shaft unit 40 with respect to each other, described hereinabove with reference to FIGS. 2A-B, facilitate the movement of filter clearing element 70 with respect to filter 50.

For some applications, such as shown in FIGS. 2A-B and 3A, filter 50 is disposed around an axis 80 of distal opening 46. For some applications, such as shown in FIGS. 2A-B and 3A, filter 50 is disposed around delivery lumen 42 in shaft unit 40.

For some applications, such as shown in FIGS. 2A-B and 3A, drainage lumen 44 is disposed around delivery lumen 42 in shaft unit 40. For other applications, such as shown in FIG. 3B, drainage lumen 44 is disposed alongside delivery lumen 42 in shaft unit 40.

Figure 4:
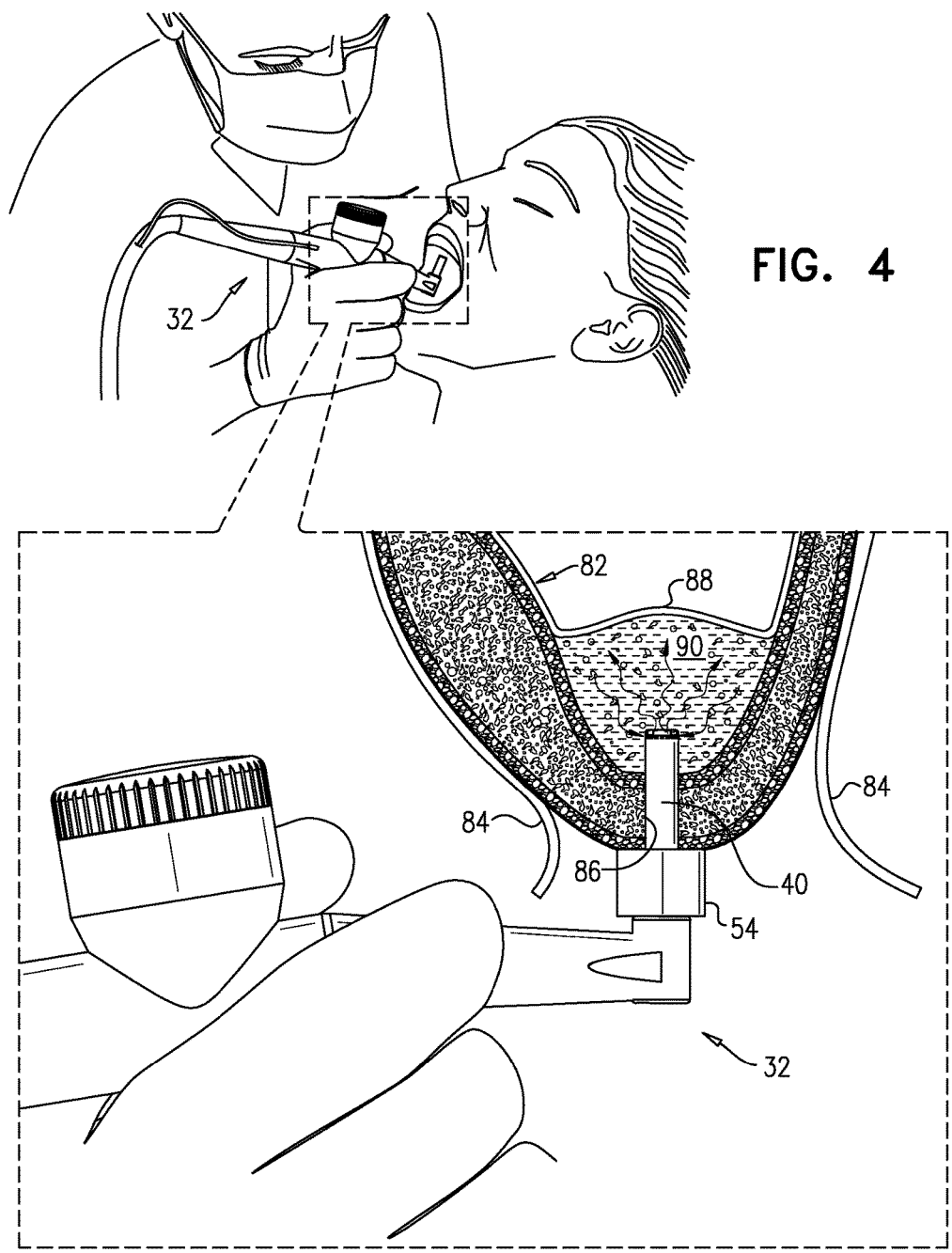
FIGS. 4 and 5A are schematic illustrations of one use of the surgical tool of FIGS. 1-3B, in accordance with an application of the present invention.
Figure 5A:
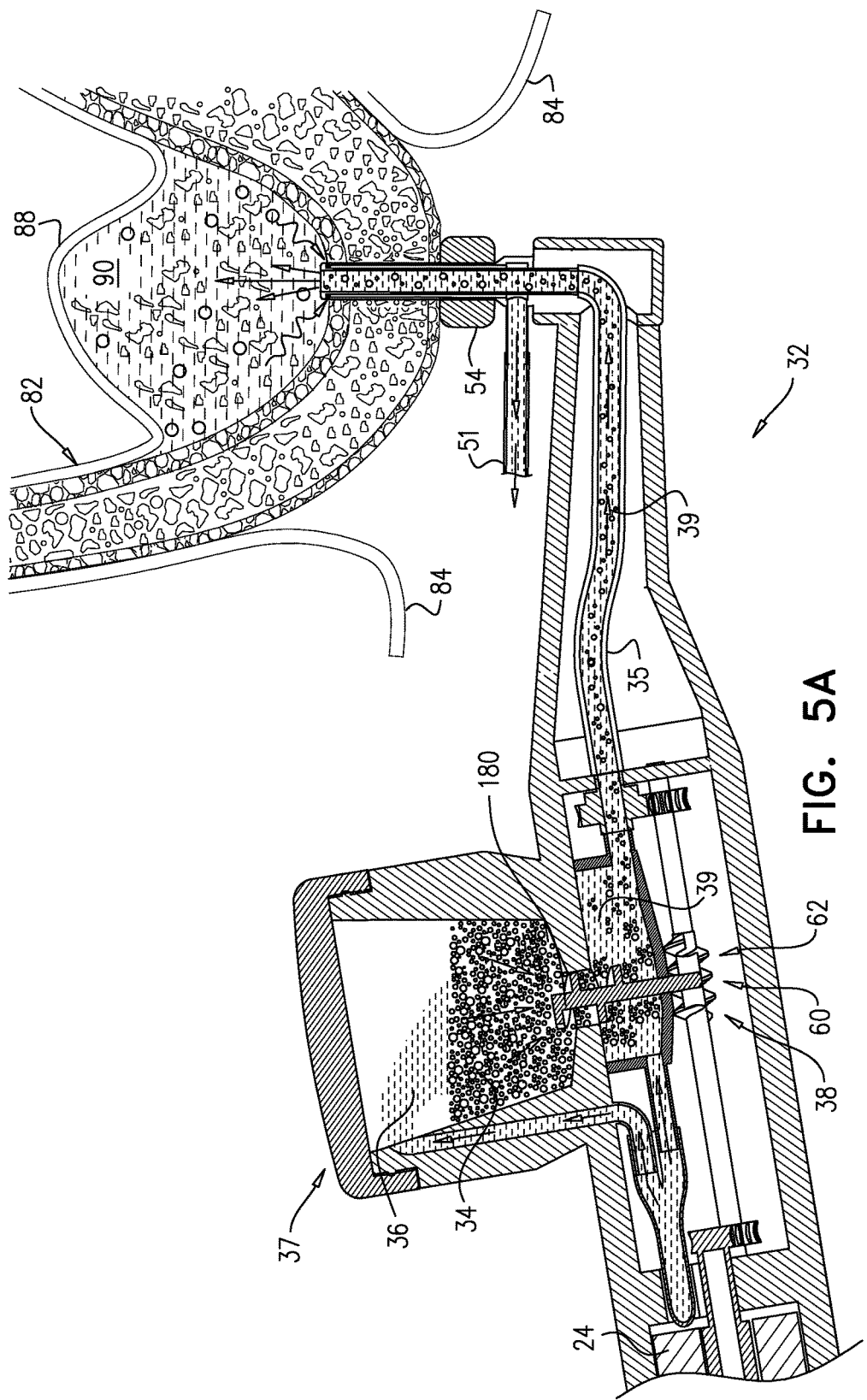

Reference is now made to FIGS. 4 and 5A, which are schematic illustrations of one use of surgical tool 20, in accordance with an application of the present invention. The illustrated use is typically performed in conjunction with a minimally-invasive closed sinus lift surgical procedure for implanting a dental implant. The procedure is typically employed when a patient's alveolar maxillary bone 82 lacks sufficient bone mass to support a conventional dental implant. The procedure may be performed using any of the techniques described in the patents and patent application publications incorporated hereinbelow by reference, or using other sinus lift techniques known in the art. For some applications, the surgeon reflects gingiva 84, exposing an occlusal surface of maxillary alveolar bone 82 as shown in FIGS. 4 and 5A. Alternatively, a flapless procedure is performed, in which the gingiva is not reflected (approach not shown). Although a crestal approach is shown, a lateral approach may alternatively be used.

A bore 86 (e.g., exactly one bore) is formed through bone 82 from a first side of the bone to a second side of the bone. A Schneiderian membrane 88 is raised to form a cavity 90 between the second side of the bone and Schneiderian membrane 88, such as using hydraulic pressure or mechanical elevation.

Exactly one shaft unit 40 is inserted, from the first side of a bone, into bore 86, such that distal opening 46 is disposed in bore 86 or in cavity 90 (in other words, distal opening 46 may or may not penetrate the sinus floor). Solid-liquid composition 39 is injected through delivery lumen 42 and distal opening 46 into cavity 90, such that (a) a portion of physiological liquid solution 36 drains through filter 50, and (b) filter 50 inhibits passage of bone graft particles 34 of solid-liquid composition 39, such that bone graft particles 34 accumulate in cavity 90, and function as regenerative material. Typically, at least 50% of physiological liquid solution 36 drains through filter 50 in a distal-to-proximal direction, optionally while solid-liquid composition 39 is being injected. Typically, 2-300 ml of solid-liquid composition 39 is injected. Typically, between 0.2 and 20 ml of bone graft particles accumulate in the cavity. Typically, but not necessarily, physiological liquid solution 36 drains through filter 50 at the same time that solid-liquid composition 39 is injected.

Alternatively, the surgeon injects solid-liquid composition 39 to lift membrane 88, thereby combining the lift and bone graft injection steps into a single step. Further alternatively, the surgeon uses surgical tool 20 to inject physiological solution, e.g., saline solution, to raise the membrane.

After solid-liquid composition 39 is injected, an implant is implanted at least partially within cavity 90, either during the same procedure or after bone grows into bone graft particles 34 in cavity 90. After bone grows into bone graft particles 34, a dental appliance, such as a crown, is coupled to the implant.

Figure 5B:
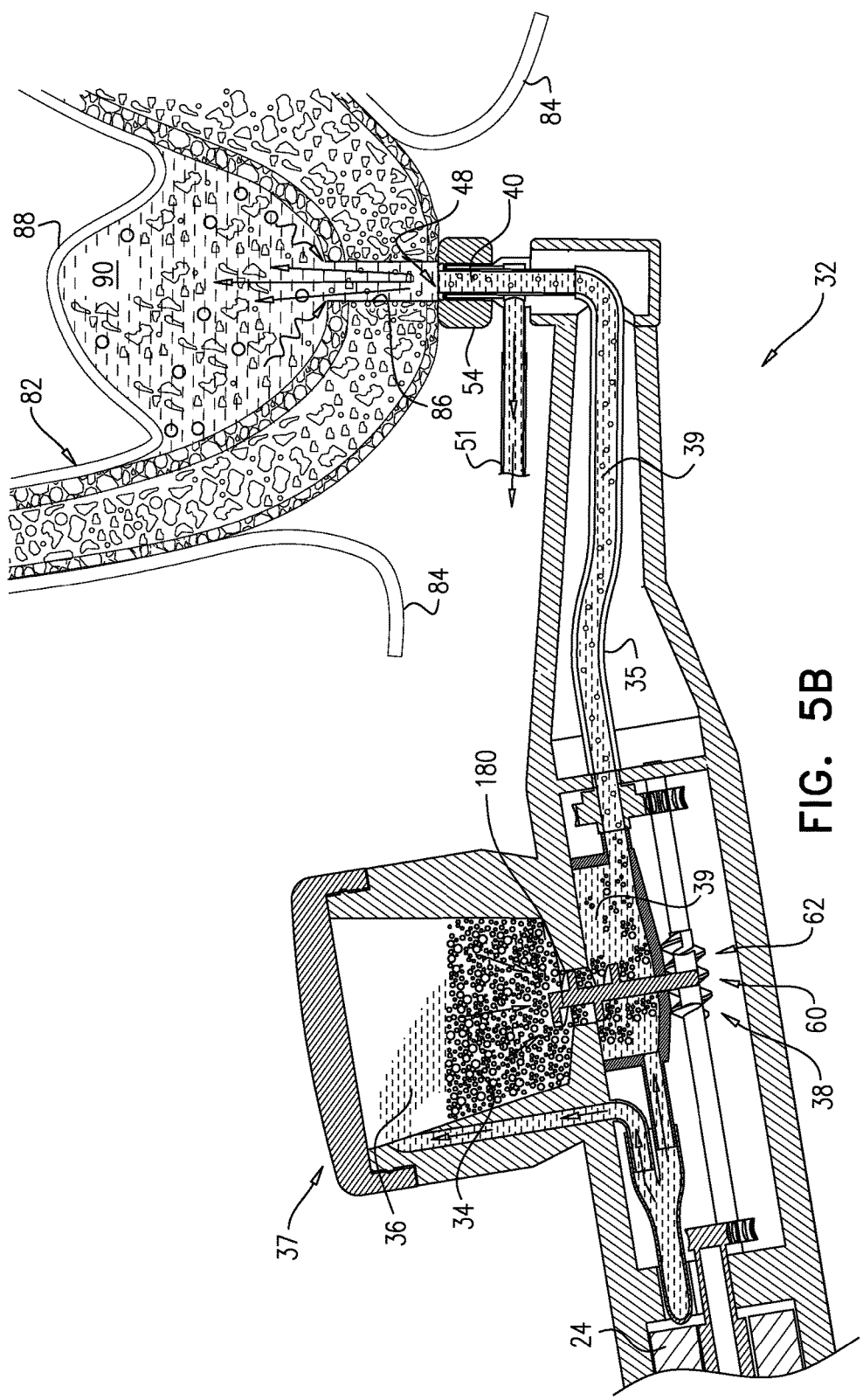
FIG. 5B a schematic illustration of an alternative configuration of a shaft unit of the surgical tool of FIGS. 1-3B and one use thereof, in accordance with an application of the present invention.

Reference is now made to FIG. 5B, which a schematic illustration of an alternative configuration of shaft unit 40 and one use thereof, in accordance with an application of the present invention. In this configuration, distal end 48 of shaft unit 40 is disposed no more distal than a distal-most surface of sealing element 54. Distal end 48 of shaft unit 40 may be either flush with the distal-most surface of sealing element 54, or recessed within sealing element 54 (i.e., proximal to the distal-most surface of sealing element 54). Because sealing element 54 forms a fluid-tight seal with the tissue (gingiva or bone) surrounding bore 86, distal opening 46 is disposed in fluid communication with bore 86 (and cavity 90), and solid-liquid composition 39, when injected through distal opening 46, flows into bore 86 and then into cavity 90. Similarly, filtered physiological liquid solution 36 passes from cavity 90, through bore 86, and into drainage lumen 44. For some applications, shaft unit 40 is not provided. Distal opening 46 may instead be provided by another portion of injector unit 32 (such as an external surface thereof), and configured to provide fluid communication with an opening through sealing element 54.

Figure 6A:
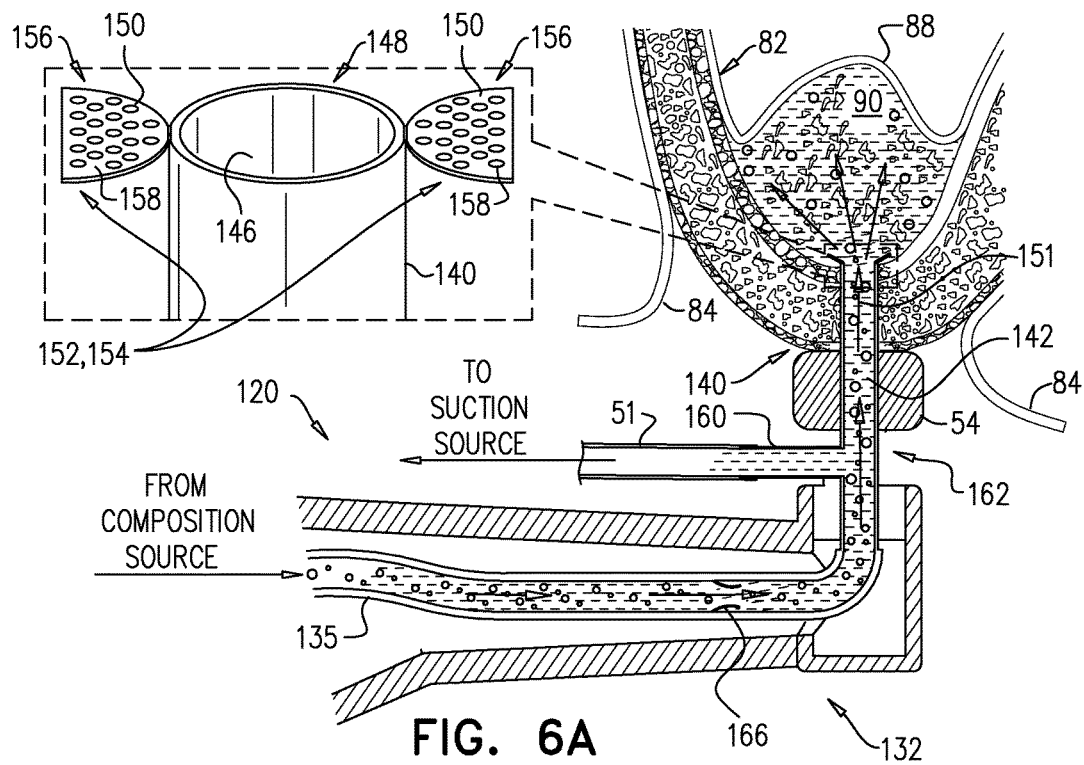
FIGS. 6A-B and 7 are schematic illustrations of another surgical tool comprising an injector unit, in accordance with an application of the present invention.
Figure 6B:
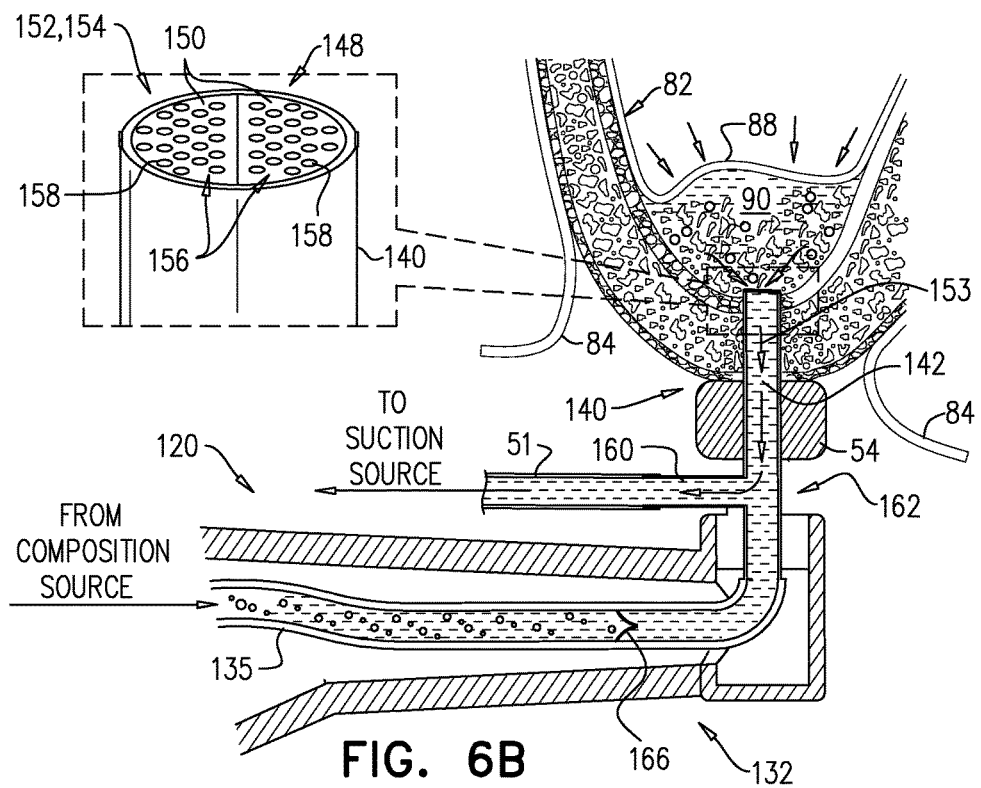
Figure 7:
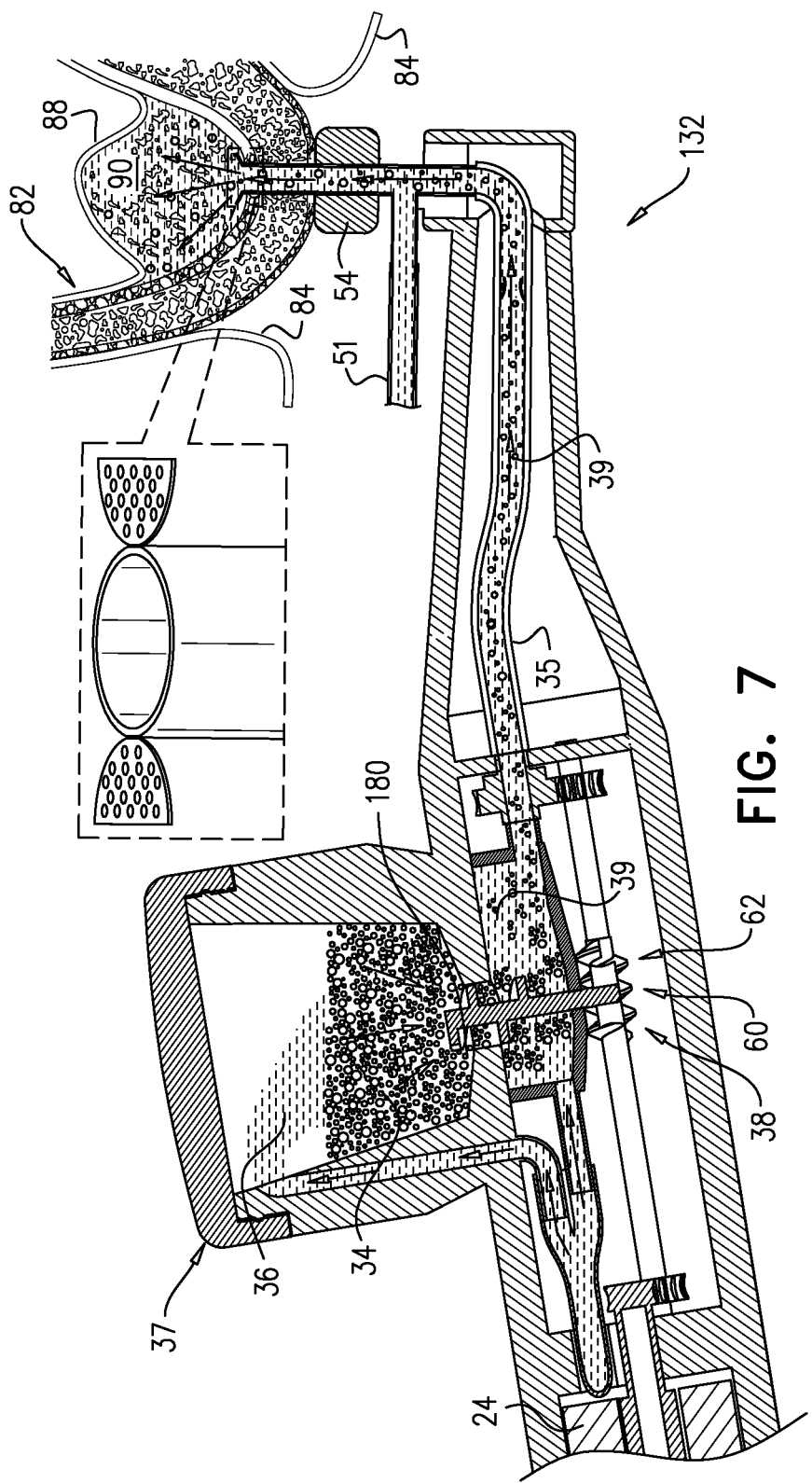

Reference is now made to FIGS. 6A-B and 7, which are schematic illustrations of a surgical tool 120 comprising an injector unit 132, in accordance with an application of the present invention. Except as described hereinbelow, surgical tool 120 and injector unit 132 are generally similar to surgical tool 20 and injector unit 32, described hereinabove with reference to FIGS. 1-3B, and may implement any of the features thereof. Surgical tool 120 (e.g., injector unit 132 thereof) comprises exactly one shaft unit 140, which is shaped so as to define a lumen 142, and a distal opening 146, which is typically disposed within 10 mm of a distal end 148 of shaft unit 140 (e.g., within 5 mm of the distal end, such as at the distal end), in fluid communication with lumen 142. Composition source 38, described hereinbelow with reference to FIGS. 2A-B, is coupled in selective fluid communication with lumen 142. As used in the present application, including in the claims, distal end 148 of shaft unit 140 means the distal-most point(s) of the shaft unit.

For some applications, shaft unit 140 is shaped so as to define exactly one lumen 142. For other applications, shaft unit 140 is shaped so as to define a plurality of lumens that are in fluid communication with one another in shaft unit 140. Typically, a largest circle circumscribed by a cross-section of lumen 142 has a diameter of at least 1 mm, such as at least 1.5 mm, and/or no more than 7 mm, such as no more than 4 mm (the cross-section is perpendicular to a longitudinal axis of the lumen).

Injector unit 132 further comprises a one-way filter 150, which is disposed in fluid communication with lumen 142, and which is configured to:
- allow passage, in a proximal-to-distal direction (schematically indicated by an arrow 151 in FIG. 6A), of bone graft particles 34 and physiological liquid solution 36 of solid-liquid composition 39,
- inhibit passage, in a distal-to-proximal direction (schematically indicated by an arrow 153 in FIG. 6B), of bone graft particles 34 of solid-liquid composition 39, and
- allow passage, in the distal-to-proximal direction, of physiological liquid solution 36 of solid-liquid composition 39.

For some applications, surgical tool 120 (e.g., injector unit 132 thereof) comprises a one-way filter valve 152 that comprises one-way filter 150. One-way filter valve 152 is in fluid communication with lumen 142. For example, one-way filter valve 152 may comprise a leaf valve 154, which comprises one or more leafs 156. For example, leafs 156 may comprise mesh 158 having openings smaller than bone graft particles 34, or may be shaped so as to define a plurality of slits having a width narrower than bone graft particles 34. For some applications, one-way filter 150 is disposed within 10 mm of distal end 148 of shaft unit 140.

Composition source 38 is coupled in fluid communication with lumen 142, such as via a feeder tube 135. For some applications, surgical tool 20 is shaped so as to define a suction port 160, and one-way filter 150 is in selective fluid communication with suction source 49 via suction port 160. For some applications, suction port 160 is disposed at a site 162 along a fluid path between one-way filter 150 and composition source 38, and surgical tool 20 (e.g., injector unit 32 thereof) further comprises a source one-way valve 166, which is disposed along the fluid path proximal to site 162 at which suction port 160 is disposed.

For some applications, the pump (e.g., pump 27 of external control unit 22, or pump 43 of injector unit 132) is configured to pump solid-liquid composition 39 through distal opening 146 via lumen 142. For some applications, the pump is configured to pump solid-liquid composition 39 with an on-off duty cycle. For some applications, suction port 160 is configured to assume an open state when the pump is off, and a closed state when the pump is on. For some applications, suction source 49 is configured to apply suction when the pump is off, and not apply the suction when the pump is on.

To inhibit suctioning of bone graft particles 34 through suction port 160, for some applications, source one-way valve 166 is configured to open at a higher pressure gradient than the pressure gradient at which one-way filter valve 152 opens (the injection pressure is typically substantially higher than the suction vacuum). Alternatively or additionally, application of the suction is synchronized with application of the pressure, so that the suction is off when the solid-liquid composition 39 is injected and vice versa.

For some applications, surgical tool 120 is used in conjunction with a minimally-invasive sinus lift surgical procedure for implanting a dental implant. Other than as described below, the procedure is similar to the procedure described hereinabove with reference to FIGS. 4 and 5A. After the bore has been formed and Schneiderian membrane 88 has been raised to form cavity 90, the exactly one shaft unit 140 is inserted, from a first side of bone 82, such that distal opening 146 is disposed in the bore or in cavity 90. Solid-liquid composition 39 is injected through lumen 142, one-way filter 150, and distal opening 146 into cavity 90, as shown in FIGS. 6A and 7. Physiological liquid solution 36 of solid-liquid composition 39 drains through one-way filter 150, as shown in FIG. 6B. Typically, at least 50% of physiological liquid solution 36 drains through filter 50 in the distal-to-proximal direction.

For some applications, injecting and draining comprise alternatingly injecting (as shown in FIGS. 6A and 7) and draining (as shown in FIG. 6B). For some applications, injecting solid-liquid composition 39 comprises pumping solid-liquid composition 39 at a positive hydraulic pressure, and draining physiological liquid solution 36 comprises suctioning physiological liquid solution 36 at a negative hydraulic pressure. For some applications, pumping and suctioning comprise alternatingly pumping and suctioning.

An implant is implanted, as described hereinabove with reference to FIGS. 4 and 5A.

For some applications, distal end 148 of shaft unit 140 is disposed no more distal than a distal-most surface of sealing element 54, such as described hereinabove with reference to FIG. 5B, mutatis mutandis. Distal end 148 of shaft unit 140 may be either flush with the distal-most surface of sealing element 54, or recessed within sealing element 54 (i.e., proximal to the distal-most surface of sealing element 54). Because sealing element 54 forms a fluid-tight seal with the tissue (gingiva or bone) surrounding bore 86, distal opening 146 is disposed in fluid communication with bore 86 (and cavity 90), and solid-liquid composition 39, when injected through distal opening 146, flows into bore 86 and then into cavity 90. Similarly, physiological liquid solution 36 passes from cavity 90, through bore 86 and one-way filter 150, and into lumen 142. For some applications, shaft unit 140 is not provided. Distal opening 146 may instead be provided by another portion of injector unit 132 (such as an external surface thereof), and configured to provide fluid communication with an opening through sealing element 54.

Reference is again made to FIGS. 2A-B, and is additionally made to FIGS. 8A-K, which are highly schematic illustrations of several configurations of mixing feeder unit 62, in accordance with respective applications of the present invention. Mixing feeder unit 62 may retrieve bone graft particles 34 from solid-particle container 37 passively (such as by gravity and/or flow of physiological liquid solution 36 through solid-particle container 37). Alternatively or additionally, mixing feeder unit 62 may retrieve bone graft particles 34 from solid-particle container 37 actively, such as using one or more of the following: vibration (in order to overcome the pressure filtration effect), ultrasonic energy, positive pressure (automatic or manual) in the container applied by physiological liquid solution 36, suction, and/or dosage-controlled portioning of bone graft particles 34 using an Archimedes screw 180 (shown in FIGS. 2A-B) or by periodically opening an exit orifice, which releases bone graft particles into the flow of physiological liquid solution 36.

FIGS. 8A-K schematically illustrate several configurations for mixing bone graft particles 34 with physiological liquid solution 36 to generate solid-liquid composition 39. By way of example and not limitation, in these figures physiological liquid solution 36 is referred to as "saline," and solid-liquid composition 39 is referred to as "mixed solution."

Figure 8A:
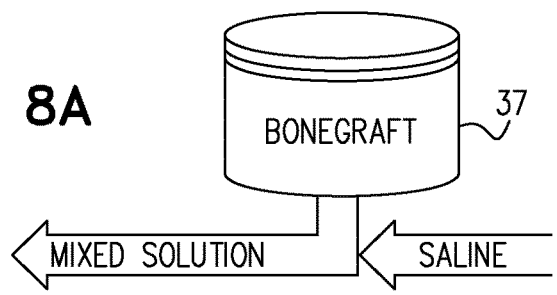
FIGS. 8A-K are highly schematic illustrations of several configurations of a mixing feeder unit, in accordance with respective applications of the present invention.

FIG. 8A illustrates passive mixing without application of pressure to physiological liquid solution 36.

Figure 8B:
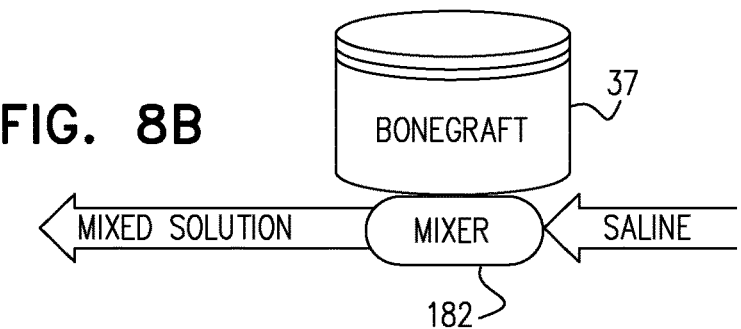

FIG. 8B illustrates active mixing (using a mixing unit 182) without application of pressure to physiological liquid solution 36.

Figure 8C:
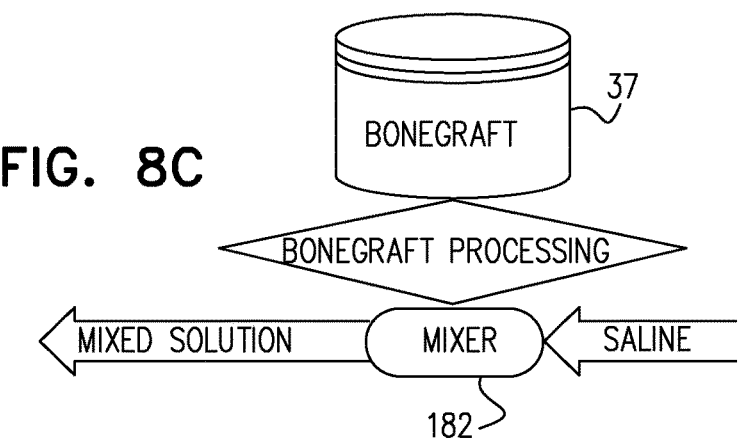

FIG. 8C illustrates active mixing (using mixing unit 182) without application of pressure to physiological liquid solution 36, with the addition of active retrieval of bone graft particles 34 from solid-particle container 37.

Figure 8D:
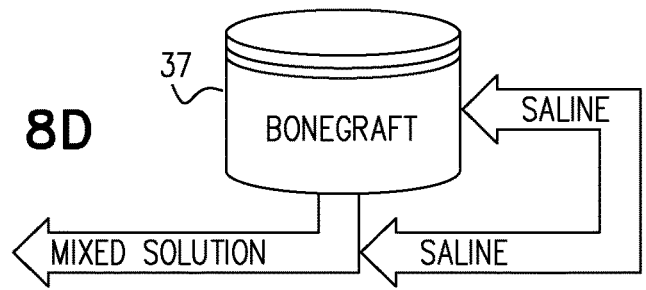

FIG. 8D illustrates passive mixing with the application of pressure to physiological liquid solution 36, and the flow of physiological liquid solution 36 through solid-particle container 37.

Figure 8E:
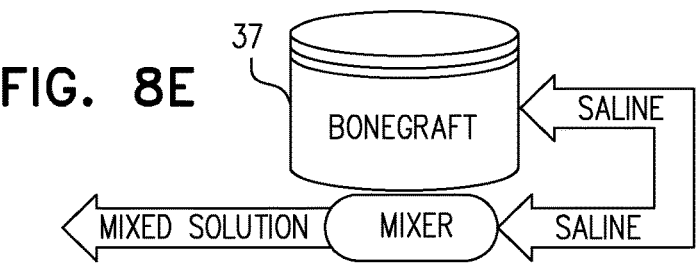

FIG. 8E illustrates active mixing (using mixing unit 182) with the application of pressure to physiological liquid solution 36, and the flow of physiological liquid solution 36 through solid-particle container 37.

Figure 8F:
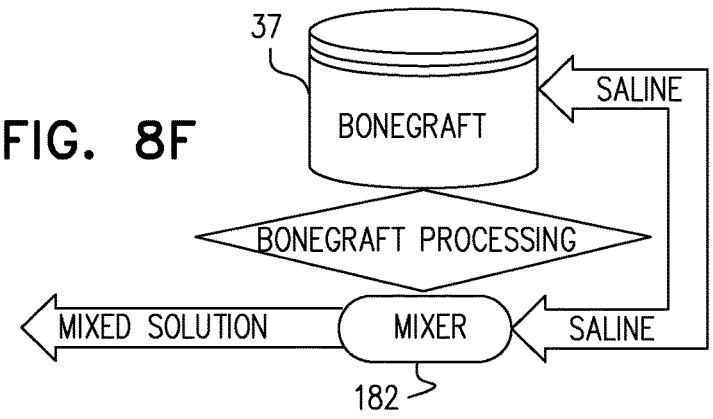

FIG. 8F illustrates active mixing (using mixing unit 182) with the application of pressure to physiological liquid solution 36, with the addition of active retrieval of bone graft particles 34 from solid-particle container 37, and the flow of physiological liquid solution 36 through solid-particle container 37.

Figure 8G:
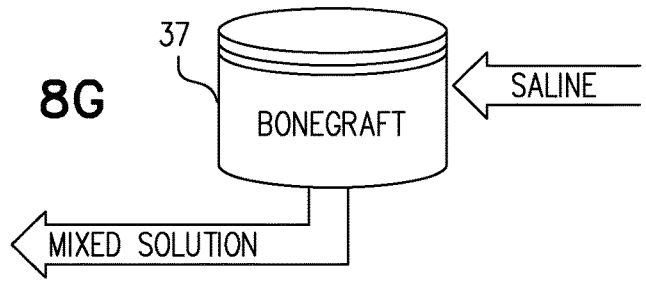

FIG. 8G illustrates passive mixing with or without application of pressure to physiological liquid solution 36, and the flow of all of physiological liquid solution 36 through solid-particle container 37.

Figure 8H:
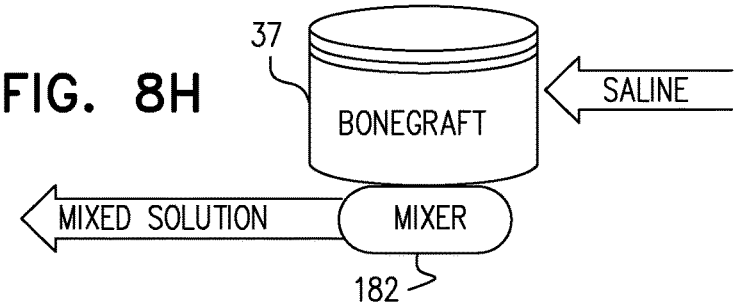

FIG. 8H illustrates active mixing (using mixing unit 182) with or without application of pressure to physiological liquid solution 36, and the flow of all of physiological liquid solution 36 through solid-particle container 37.

Figure 8I:
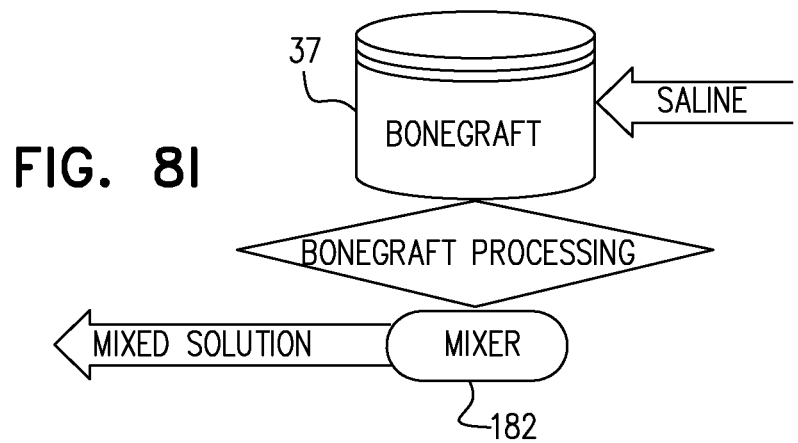

FIG. 8I illustrates active mixing (using mixing unit 182) without the application of pressure to physiological liquid solution 36, with the addition of active retrieval of bone graft particles 34 from solid-particle container 37, and the flow of all of physiological liquid solution 36 through solid-particle container 37.

Figure 8J:
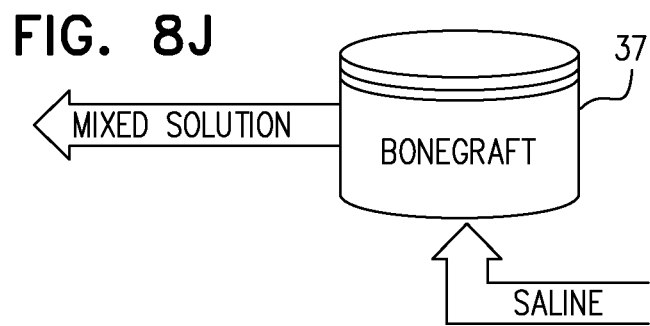

FIG. 8J illustrates the reverse flow of all of physiological liquid solution 36 through solid-particle container 37; the flow against gravity minimizes the pressure filtration effect.

Figure 8K:
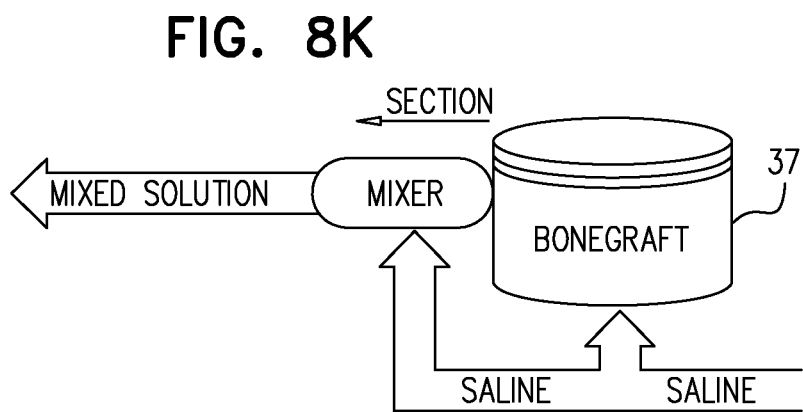

FIG. 8K illustrates the reverse flow of physiological liquid solution 36 through solid-particle container 37, with the addition of application of suction for active retrieval of bone graft particles 34 and physiological liquid solution 36 from solid-particle container 37, and active mixing (using mixing unit 182).

Reference is now made to FIGS. 9A-D, which are schematic illustrations of several configurations of an osteotome 200, in accordance with respective applications of the present invention. Osteotome 200 is configured to be used with bone graft particles 34 and a physiological liquid solution 36, such as saline solution or blood, in a manner similar to surgical tool 20, described hereinabove with reference to FIGS. 1-5B and 8A-K. For some applications, osteotome 200 is configured as a dental osteotome.

Osteotome 200 is shaped so as to define:
- a lumen 210 through osteotome 200. A distal end 212 of lumen 210 opens through a distal opening 214 disposed within 10 mm of a distal end 216 of osteotome 200, such as within 5 mm of distal end 216, e.g., at distal end 216. A proximal end 218 of lumen 210 opens through a proximal opening 220 disposed at least 5 mm proximal to distal opening 214. For some applications, proximal opening 220 is disposed within 10 mm of a proximal end 222 of osteotome 200, such as within 5 mm of proximal end 222, e.g., at proximal end 222,
- a lateral external surface 230, at least a portion of which is shaped so as to define a screw thread 232 that (a) has a distal thread end 234 that is disposed within 10 mm of distal end 216 of osteotome 200, such as within 5 mm of distal end 216, e.g., within 1 mm of distal end 216, and (b) comprises one or more raised helical ribs 236 going around osteotome 200, and
- one or more longitudinal drainage slots 250, which extend along at least respective longitudinal portions 252 of osteotome 200 having respective longitudinal lengths L of at least 5 mm, such as at least 8 mm, e.g., at least 10 mm, such as at least 12 mm, measured parallel to a central longitudinal axis 253 of osteotome 200 (typically, the longitudinal lengths L are no more than 20 mm).

As used in the present application, including in the claims, distal end 216 of osteotome 200 means the distal-most point(s) of the osteotome. Similarly, proximal end 222 of osteotome 200 means the proximal-most point(s) of the osteotome.

Typically, a largest circle circumscribed by a cross-section of lumen 210 has a diameter of at least 1 mm, such as at least 1.5 mm, and/or no more than 7 mm, such as no more than 4 mm (the cross-section is perpendicular to central longitudinal axis 253).

For some applications, the longitudinal lengths L of the respective longitudinal portions 252 are at least 2 mm greater than a thickness of bone 82 adjacently surrounding bore 86. This provides for 1 mm of longitudinal draining slots on the top and the bottom of the bone.

FIGS. 9A-D show four different configurations 200A, 200B, 200C, and 200D of osteotome 200. For some applications, such as in all of the configurations shown, at least one of the one or more longitudinal drainage slots 250 reaches proximal end 222 of osteotome 200. Alternatively, at least one of the one or more longitudinal drainage slots 250 does not reach proximal end 222 of osteotome 200 (configuration not shown).

Figure 9A:
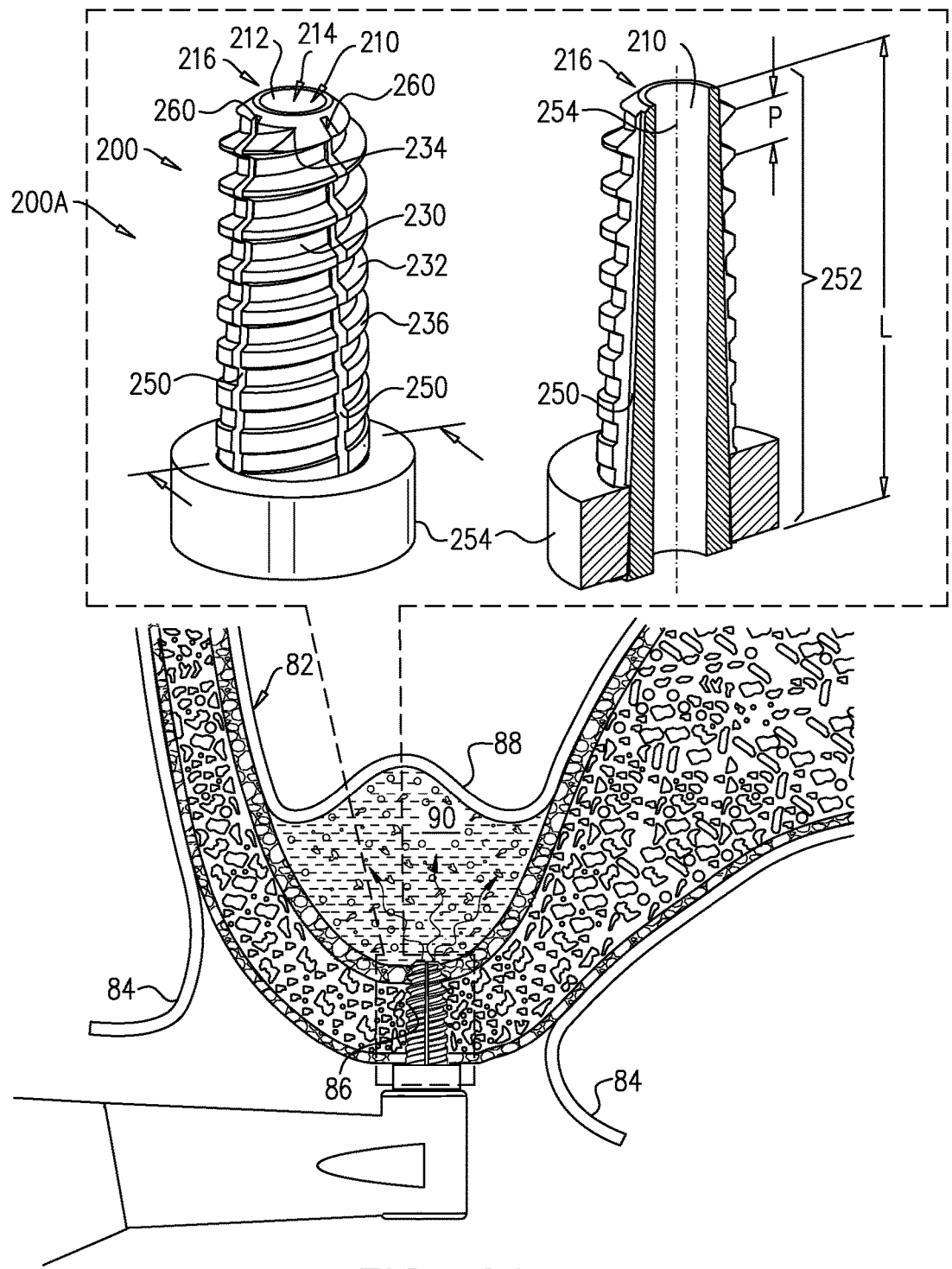
FIGS. 9A-D are schematic illustrations of several configurations of an osteotome, in accordance with respective applications of the present invention.
Figure 9B:
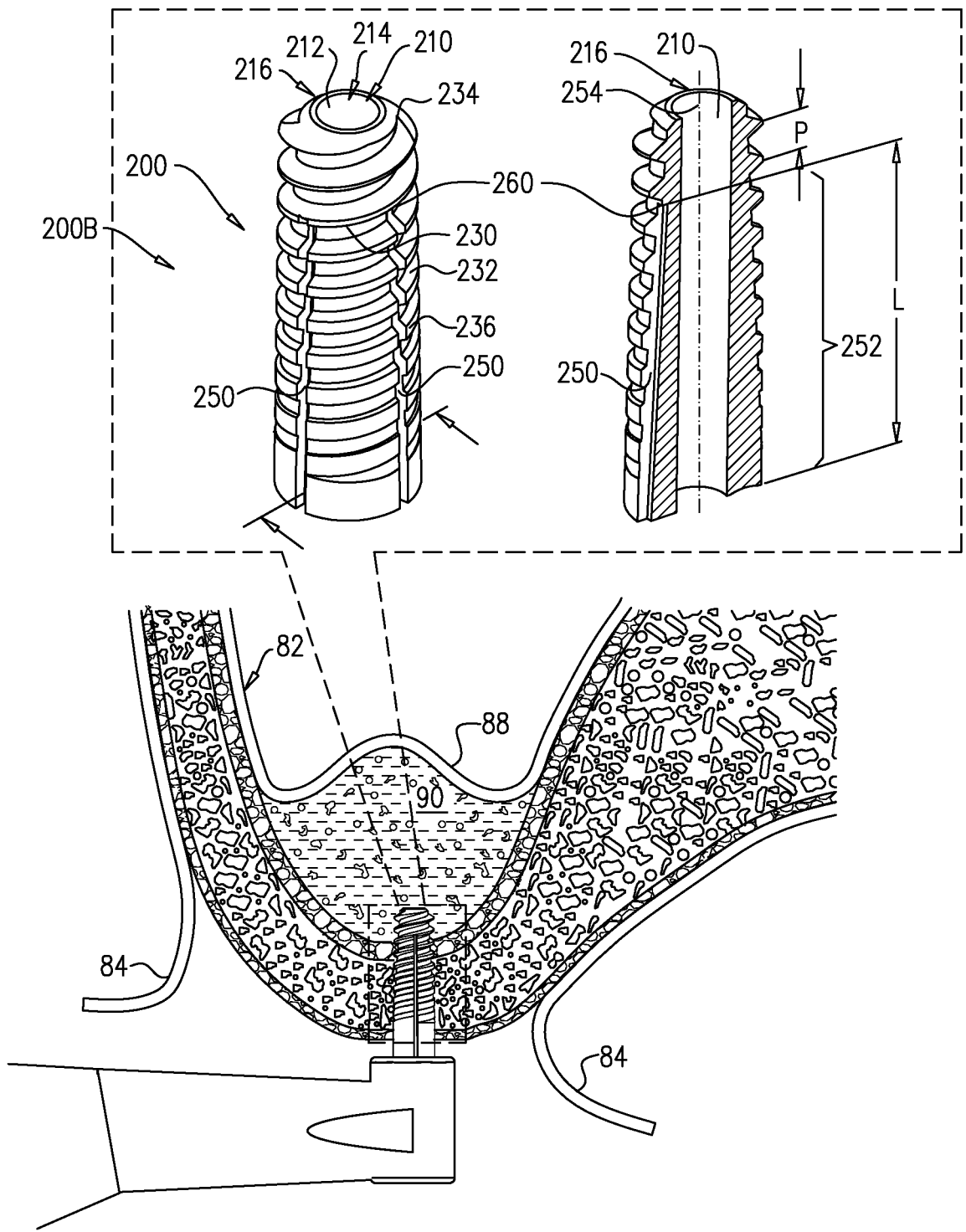
Figure 9C:
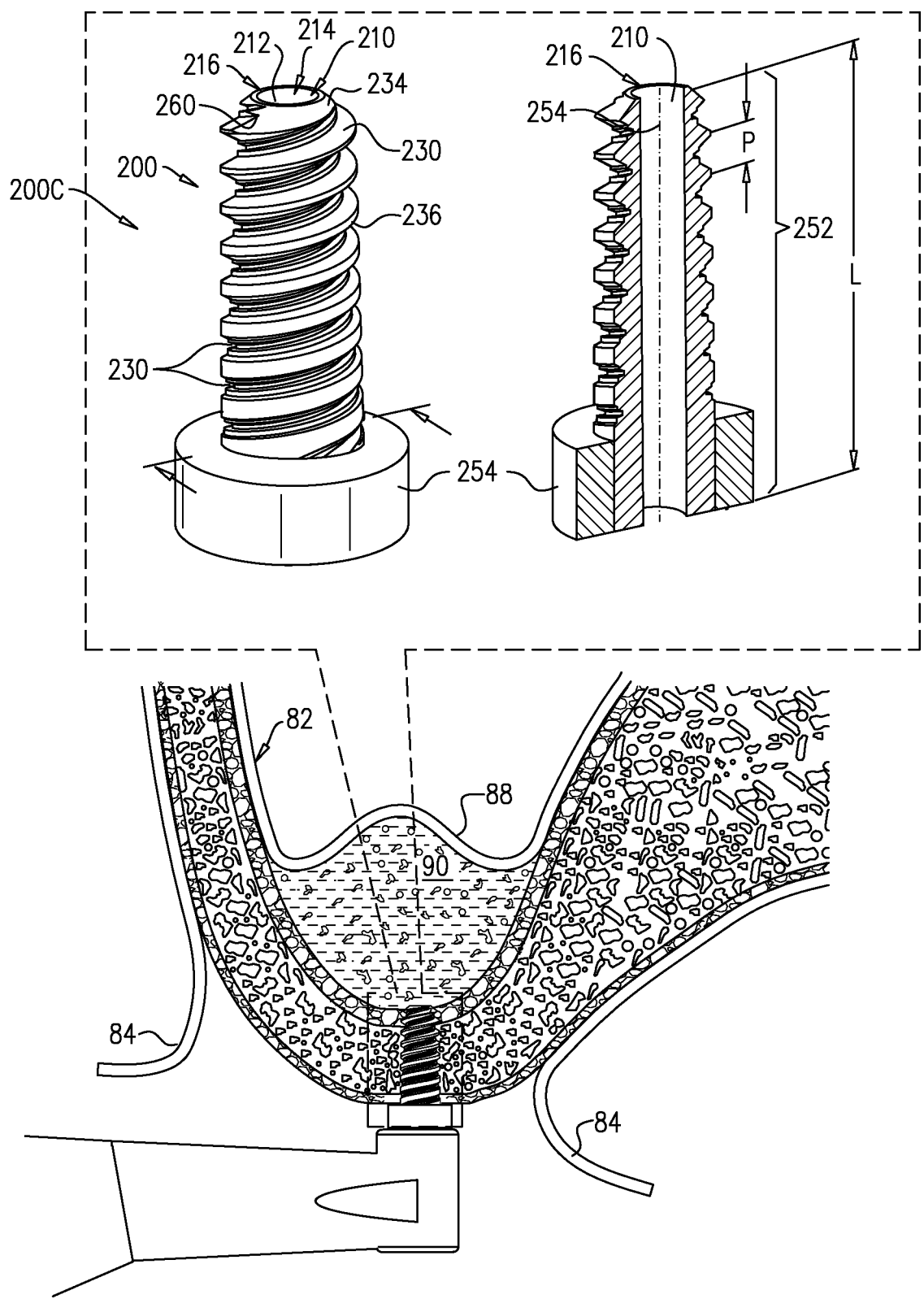
Figure 9D:
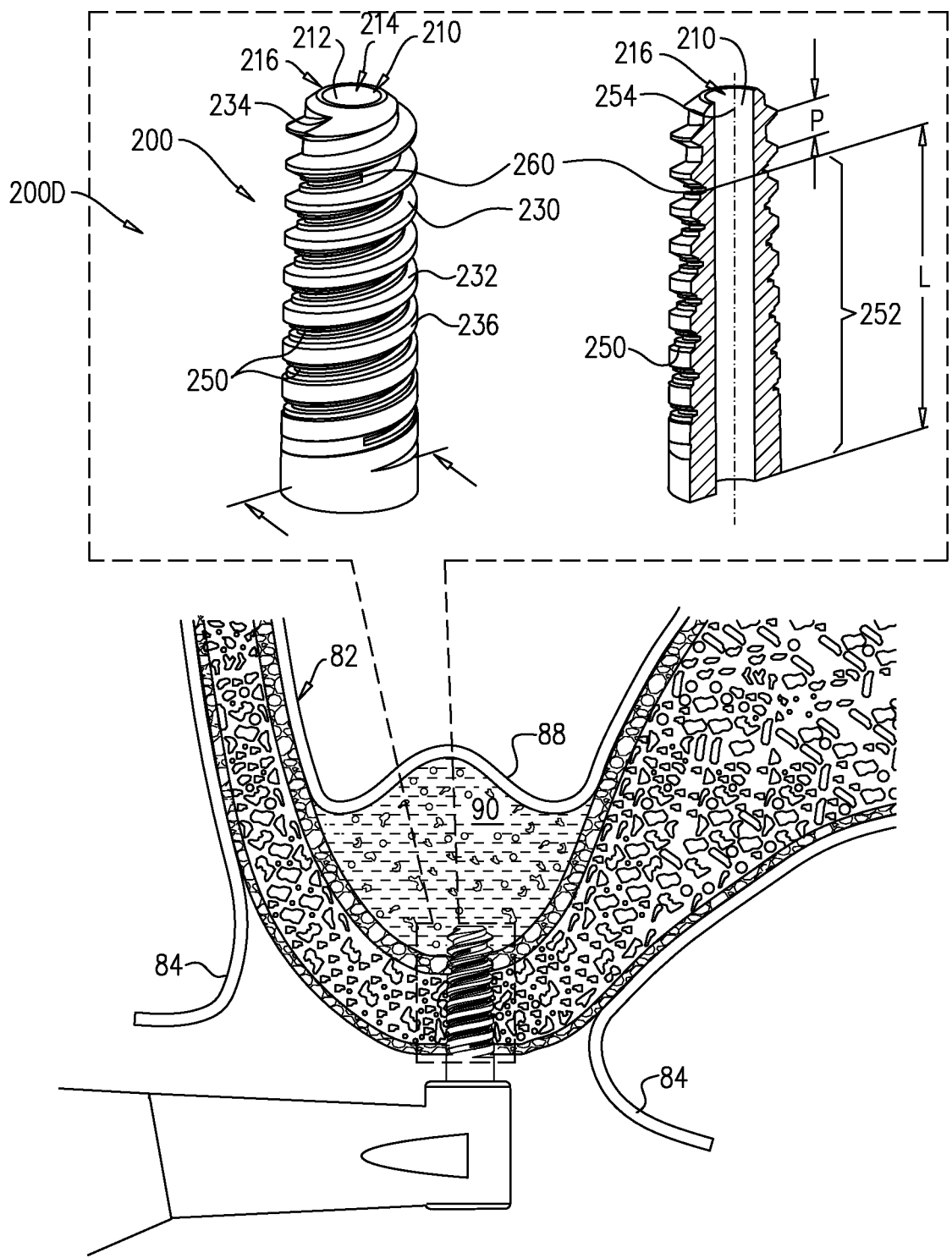

For some applications, such as in configurations 200B and 200D shown in FIGS. 9B and 9D, respectively, respective distal ends 260 of the one or more longitudinal drainage slots 250 are disposed at least one pitch P of the screw thread from distal thread end 234, such as at least two pitches P of the screw thread from distal thread end 234, or at least three pitches P of the screw thread from distal thread end 234. For some applications, such as in configurations 200B and 200D shown in FIGS. 9B and 9D, respectively, respective distal ends 260 of the one or more longitudinal drainage slots 250 are disposed at least 1.5 mm from distal end 216 of osteotome 200, such as at least 4 mm from distal end 216 of osteotome 200. For some applications, osteotome 200 further comprises a sealing element 254 disposed around an external surface of osteotome 200, and configured to form a liquid-tight seal with tissue (gingiva 84 or bone 82) around and outside bore 86 when osteotome 200 is inserted into bore 86. Sealing element 254 may be particularly useful in configurations 200A and 200C, but may also be provided in the other configurations.

For some applications, screw thread 232 is multi-start, i.e., is shaped to define more than one start, as is known in the screw art. For example, screw thread 232 may be double-start (as shown in FIGS. 9A-D), triple-start, or quadruple-start. It is noted that the pitch P of a multi-start screw is measured between axially-adjacent rib portions, even thought the rib portions are from different ribs, as is known in the screw art.

For some applications, respective average widths of the one or more longitudinal drainage slots 250 are no more than 3 mm, such as no more than 2 mm, e.g., no more than 1.5 mm or 1 mm. Typically, the widths of the one or more longitudinal drainage slots 250 are selected to be smaller than the bone graft particles 34, in order to filter the bone graft particles 34 (i.e., inhibit their passage through the drainage slots).

For some applications, respective average depths of the one or more longitudinal drainage slots 250, measured with respect to an outermost portion of screw thread 232 (i.e., locally with respect to the outermost portion of the screw thread; the width of the screw thread may vary therealong), are at least 10% greater than an average depth of screw thread 232, and/or at least 0.1 mm (such as at least 0.3 mm, e.g., at least 0.5 mm) greater than the average depth of screw thread 232, and/or at least 0.4 mm from the outermost portion of screw thread 232. (Typically, the average thread depth of screw thread 232 is at least 0.1 mm, such as at least 0.3 mm.)

For some applications, such as in configurations 200A and 200B shown in FIGS. 9A and 9B, respectively, the one or more longitudinal drainage slots 250 cross the one or more ribs 236 respective pluralities of times. For some of these applications, the one or more longitudinal drainage slots 250 comprise two or more longitudinal drainage slots 250, such as two, three, four, five, six, or more than six slots 250. For some of these applications, the one or more longitudinal drainage slots 250 are parallel to central longitudinal axis 253. For some of these applications, the one or more longitudinal drainage slots 250 helically go around the dental osteotome (a) either in the same or opposite direction as screw thread 232, with a slot pitch greater than a thread pitch of screw thread 232, such as at least 1.5 times the thread pitch, or (b) in the opposite direction as screw thread 232 (in which case the slot pitch is not necessarily greater than the thread pitch of screw thread 232). For some applications, the slot pitch equals at least the quotient of (a) 2 mm divided by (b) the number of starts of screw thread 232. (Typically, the thread pitch is at least the quotient of (a) 1 mm (e.g., 1.2 mm, such as 2 mm) divided by (b) the number of starts of screw thread 232.)

For other applications, such as in configurations 200C and 200D shown in FIGS. 9C and 9D, respectively, screw thread 232 has one or more starts and a corresponding number of roots, and osteotome 200 is shaped so as to define a number of longitudinal drainage slots 250 that corresponds to a number of the starts of screw thread 232, and which are disposed within the one or more roots of screw thread 232, respectively, typically at the deepest part of the roots (and thus follow the helical path of screw thread 232 around the osteotome). For some of these applications, as in configuration 200D shown in FIG. 9D, distal end 260 of longitudinal drainage slot 250 is disposed at least one pitch P of screw thread 232 from distal thread end 234, such as at least two pitches P of screw thread 232 from distal thread end 234, e.g., at least three pitches P of screw thread 232 from distal thread end 234.

Typically, osteotome 200 is configured to be used with bone graft particles 34 and physiological liquid solution 36, as described hereinabove. During use, osteotome 200 is inserted, from a first side of bone 82, into bore 86, such that distal opening 214 is disposed in the bore or in a cavity adjacent to the second side of the bone. A solid-liquid composition 39 of bone graft particles 34 and physiological liquid solution 36 is provided from composition source 38 that is coupled in fluid communication with lumen 210. Solid-liquid composition 39 is injected through lumen 210 and distal opening 214 into cavity 90, such that (a) a portion of physiological liquid solution 36 drains through the one or more longitudinal drainage slots 250, and (b) the one or more longitudinal drainage slots 250 inhibit passage of bone graft particles 34 of solid-liquid composition 39 such that the bone graft particles 34 accumulate in cavity 90.

For some applications, osteotome 200 is configured as a dental osteotome, and bone 82 is a bone of a jaw. For some applications, cavity 90 is between the second side of bone 82 and a membrane, such as Schneiderian membrane 88. Typically, before inserting osteotome 200, the membrane is raised to form cavity 90 between the second side of bone 82 and membrane 88.

Typically, proximal end 222 of osteotome 200 is shaped so as to define a coupling interface, such as a male or female coupling interface, which, for example, may be shaped so as to define a male or female polygon having four or more sides, such as five or more sides, or six or more sides, e.g., exactly four, five, or six sides. The surgeon may use a conventional dental wrench or dental drill to engage the coupling interface and rotate the osteotome.

Reference is now made to FIGS. 10A-D, which are schematic illustrations of a portion of a sinus lift and bone graft injection procedure performed using configuration 200B of osteotome 200, in accordance with an application of the present invention. The same method may be used with configuration 200D, mutatis mutandis. As mentioned above, in configurations 200B and 200D, shown in FIGS. 9B and 9D, respectively, respective distal ends 260 of the one or more longitudinal drainage slots 250 are disposed at least one pitch P of screw thread 232 from distal thread end 234.

Figure 10A:
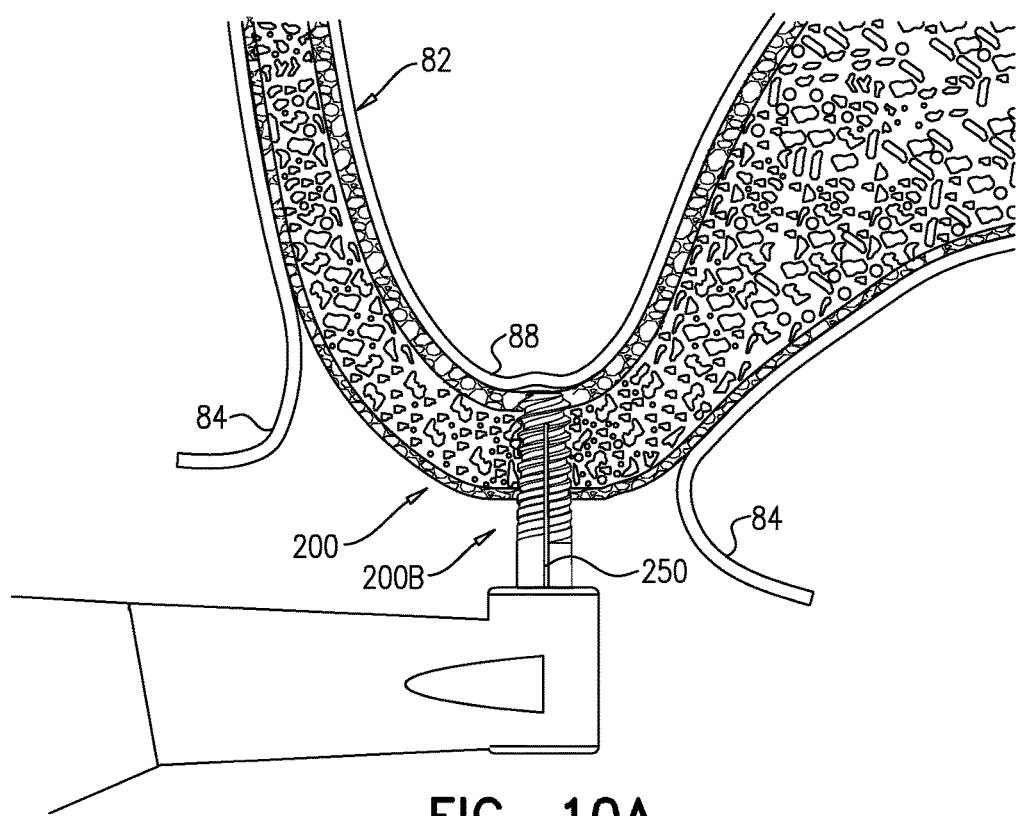
FIGS. 10A-D are schematic illustrations of a portion of a sinus lift and bone graft injection procedure performed using the configuration of the osteotome of FIG. 9B, in accordance with an application of the present invention.
Figure 10B:
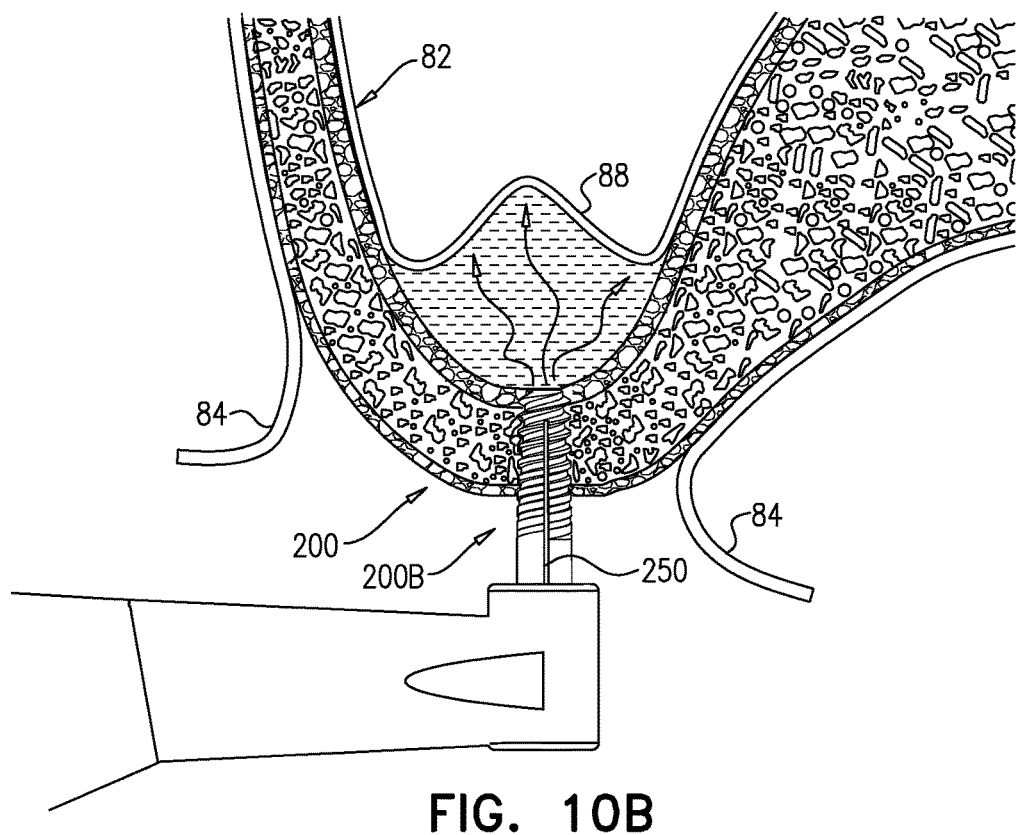

The procedure begins as described hereinabove with reference to FIGS. 4 and 5A, including forming bore 86 (e.g., exactly one bore) through bone 82 from a first side of bone 82 to a second side of bone 82 (steps not shown). Thereafter, membrane 88 is raised by (a) advancing osteotome 200 into bore 86 such that a portion of screw thread 232 distal to respective distal ends 260 of the one or more longitudinal drainage slots 250 sealingly engages a wall of bore 86, such as shown in FIG. 10A, and (b) thereafter, injecting a physiological fluid (e.g., saline solution) through the bore under sufficient pressure to raise membrane 88, such as shown in FIG. 10B. Such raising may be performed using any of the techniques described in the patents and patent application publications incorporated hereinbelow by reference, or using other hydraulic pressure sinus lift techniques known in the art.

Figure 10C:
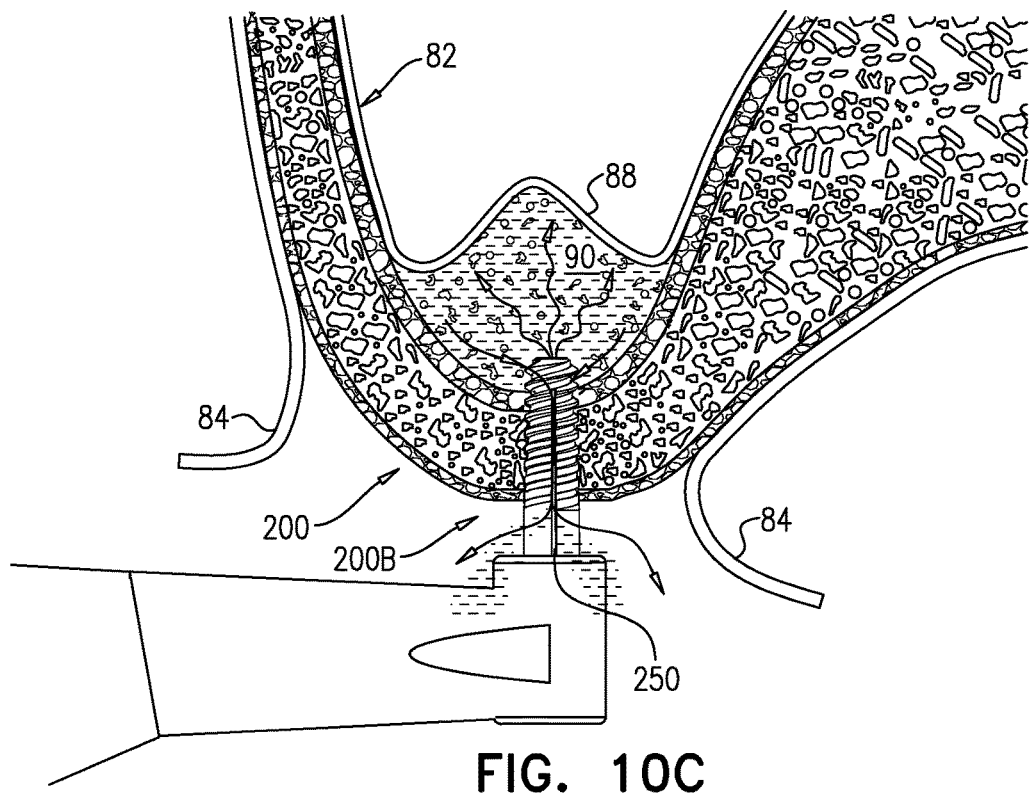
Figure 10D:
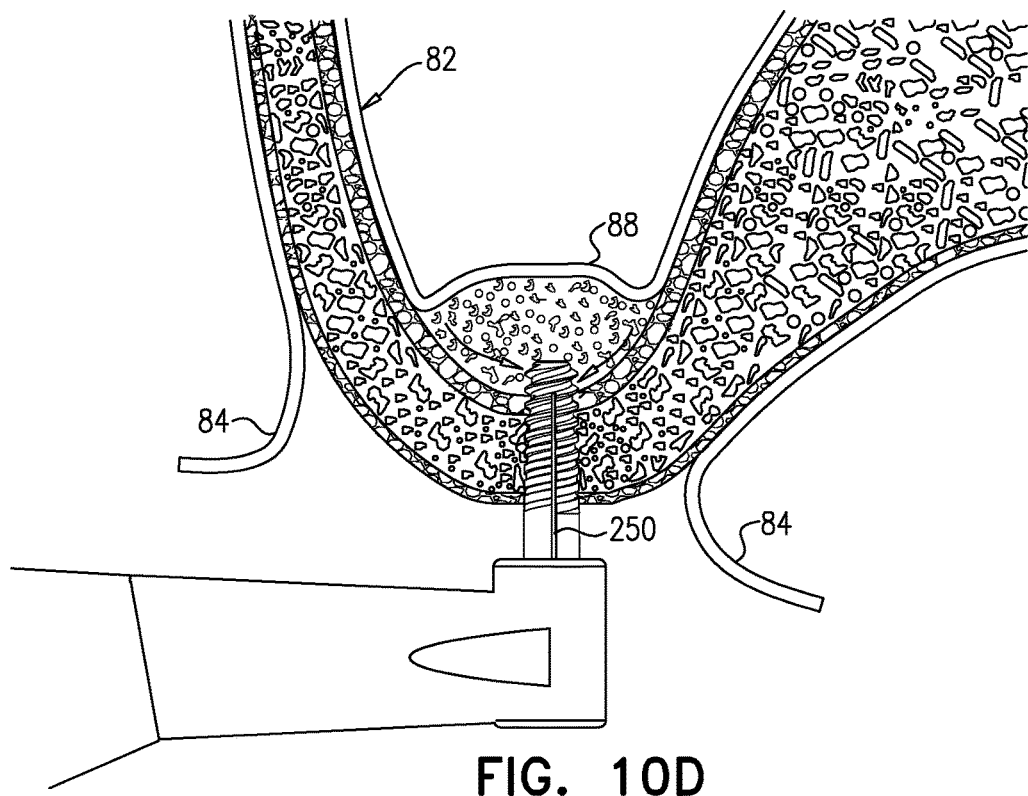

As shown in FIG. 10C, osteotome 200 is further advanced into bore 86 until the one or more drainage slots 250 come into fluid communication with cavity 90. As shown in FIG. 10D, solid-liquid composition 39 is injected into cavity 90, such as described above. For some applications, the drained physiological liquid solution may be suctioned using a conventional dental suction tool, or sealing element 254 may provided with a collecting chamber that is coupled to suction. Typically, after injecting the solid-liquid composition, an implant is implanted at least partially within cavity (step not shown).

Although the surgical tools and methods described herein have been generally described for sinus lift dental applications, these tools and methods may additionally be used for other dental applications, such as ridge augmentation (in both the maxilla and mandible) (such as by injecting the solid-liquid composition between the gingiva and the bone crest), or sinus floor elevation. In addition, these tools and methods may additionally be used for non-dental applications, such as orthopedic applications. For orthopedic applications, bone graft particles 34 may have a larger average particle size, e.g., up to 7 mm.

Reference is now made to FIG. 11, which is a schematic illustration of one use of surgical tool 20 for ridge augmentation, in accordance with an application of the present invention. In this application, surgical tool 20, described hereinabove with reference to FIGS. 1-5B and 8A-K, is used to perform ridge augmentation of a jaw bone 300 (either a mandible or a maxilla). For some applications, gingiva 384 is dissected from jaw bone 300, such as by tunneling, as is known in the art. Optionally, a structural support 386 is placed under gingiva 384; for example, structural support 386 may comprise a mesh, reinforced membrane, and/or stent. Bone graft injector unit 32 of surgical tool 20 is used to inject solid-liquid composition 39 between jaw bone 300 and gingiva 384, or between jaw bone 300 and structural support 386. Alternatively, surgical tool 120, described hereinabove with reference to FIGS. 6A-B, 7, and 8A-K, is used to perform this procedure.

Reference is now made to FIGS. 12A-B, which are schematic illustrations of one use of surgical tool 20 for performing a minimally-invasive spinal interbody fusion, in accordance with an application of the present invention. The approach to the spine (anterior, posterior, or lateral) depends on the site (e.g., lumbar, cervical, or thoracic spine). Typically, an inner vertebral disc is removed or partially removed and replaced with a structural support 400, such as a rigid cage. Bone graft injector unit 32 of surgical tool 20, described hereinabove with reference to FIGS. 1-5B and 8A-K, is used to inject solid-liquid composition 39 into structural support 400. Optionally, external fixation is also performed to fixate the adjacent vertebrae, as is known in the art, such as shown in FIG. 12B. For this application, shaft unit 40 is generally coaxial with the body of bone graft injector unit 32, i.e., faces forward rather than sideways; shaft unit 40 may also be somewhat longer than in the configurations shown in FIGS. 1-5B. Alternatively, surgical tool 120, described hereinabove with reference to FIGS. 6A-B, 7, and 8A-K, is used to perform this procedure, mutatis mutandis.

Figure 13:
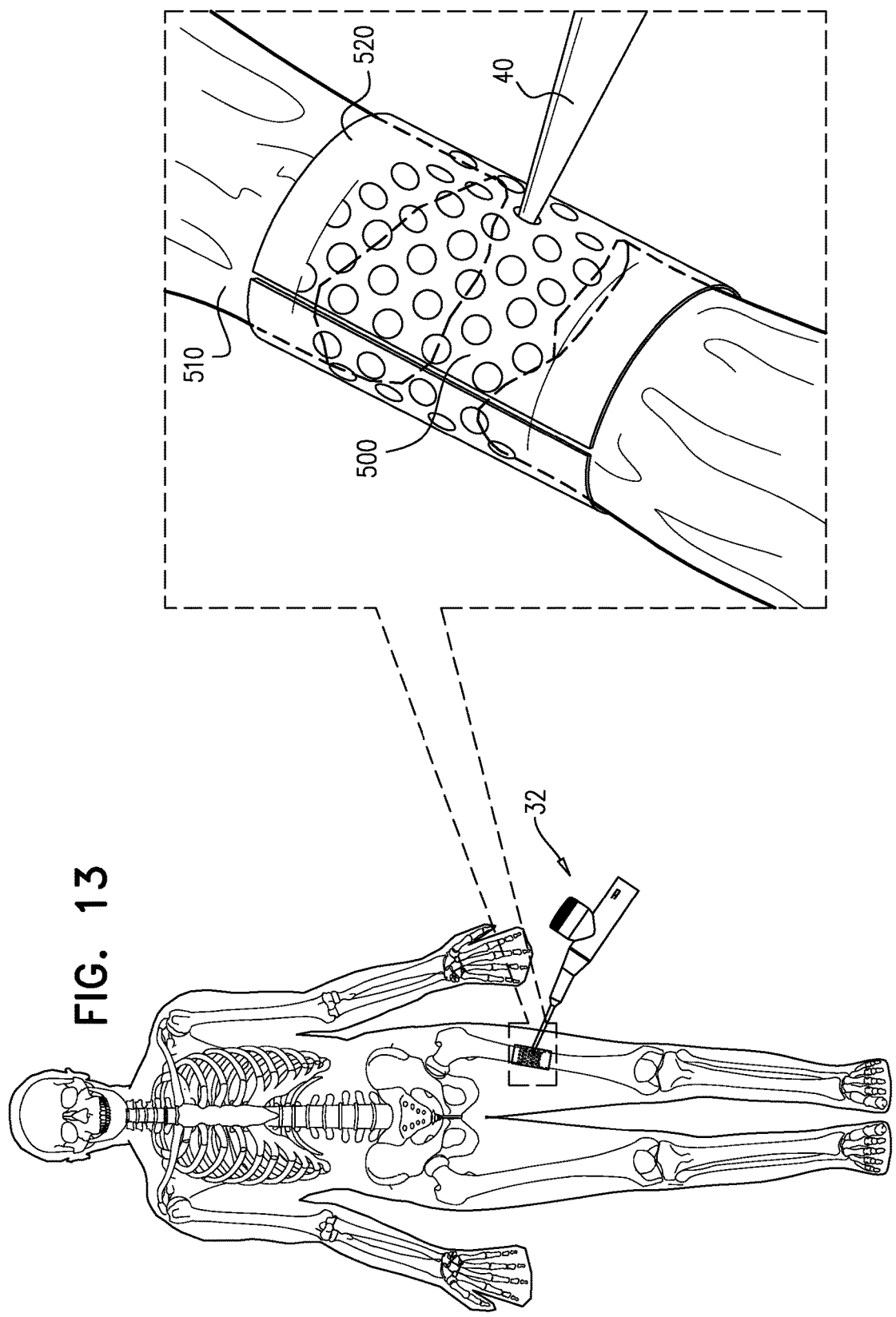
FIG. 13 is a schematic illustration of one use of the surgical tool of FIGS. 1-5B for filling a bone defect, in accordance with an application of the present invention.

Reference is now made to FIG. 13, which is a schematic illustration of one use of surgical tool 20 for filling a bone defect, in accordance with an application of the present invention. In this application, surgical tool 20, described hereinabove with reference to FIGS. 1-5B and 8A-K, is used to fill a defect 500 in a bone 510. This technique may be used for orthopedic procedures, as well as for dental procedures. For some applications, a structural element 520, such as a crib, is placed over defect 500 in order to define a volume to be filled. Bone graft injector unit 32 of surgical tool 20 is used to inject solid-liquid composition 39 into the volume defined by structural element 520. As described hereinabove with reference to FIGS. 12A-B, for this application, shaft unit 40 is generally coaxially with the body of bone graft injector unit 32, and be longer than in the configurations shown in FIGS. 1-5B. Alternatively, surgical tool 120, described hereinabove with reference to FIGS. 6A-B, 7, and 8A-K, is used to perform this procedure, mutatis mutandis.

Although the techniques described herein have been generally described for use with bone graft particles, these techniques may also be used with other solid particles, such as, as for example, drug-releasing solid particles or solid drug particles.

The scope of the present invention includes embodiments described in the following patents and patent application publications, which are assigned to the assignee of the present application and are incorporated herein by reference. In an embodiment, techniques and apparatus described in one or more of the following patents or patent application publications are combined with techniques and apparatus described herein:

U.S. Pat. No. 7,934,929 to Better et al.
U.S. Pat. No. 8,029,284 to Better et al.
U.S. Pat. No. 8,662,891 to Uchitel et al.
U.S. Pat. No. 8,388,343 to Better et al.
U.S. Pat. No. 8,702,423 to Better et al.
PCT Publication WO 2010/035270 to Better et al.
PCT Publication WO 2010/146573 to Better et al.
PCT Publication WO 2014/199332 to Fostick et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   injecting, during a dental procedure, from a first side of a bone, through (a) exactly one bore that passes through the bone from the first side to a second side of the bone, and (b) into a cavity adjacent to the second side of the bone, a solid-liquid composition of solid particles and a physiological liquid solution; and
   draining, during the dental procedure, the physiological liquid solution from the cavity and through the bore while inhibiting passage of the solid particles of the solid-liquid composition, such that the solid particles accumulate in the cavity,
   wherein injecting the solid-liquid composition comprises pumping the solid-liquid composition at a pulsating hydraulic pressure that periodically varies between positive and negative.

2. The method according to claim 1, wherein inhibiting the passage of the solid particles comprises using a filter to inhibit the passage of the solid particles.

3. The method according to claim 2, wherein injecting the solid-liquid composition comprises injecting the solid-liquid composition such that at least 50% of the physiological liquid solution drains through the filter in a distal-to-proximal direction.

4. The method according to claim 1, wherein injecting the solid-liquid composition comprises injecting 2-300 ml of the solid-liquid composition.

5. The method according to claim 1, wherein the cavity is between the second side of the bone and a membrane.

6. The method according to claim 5, further comprising, before injecting the solid-liquid composition, raising the membrane to form the cavity between the second side of the bone and the membrane.

7. The method according to claim 5, wherein the membrane is a Schneiderian membrane.

8. The method according to claim 1, further comprising, after injecting the solid-liquid composition, implanting an implant at least partially within the cavity.

9. The method according to claim 1, wherein the solid particles are solid bone graft particles, and wherein injecting comprises injecting the solid-liquid composition of the solid bone graft particles and the physiological liquid solution.

10. The method according to claim 1, wherein draining the physiological liquid solution comprises suctioning the physiological liquid solution at a negative hydraulic pressure.

11. The method according to claim 1, wherein injecting the solid-liquid composition comprises activating a combining unit to provide the solid-liquid composition by combining the solid particles with the physiological liquid solution.

12. The method according to claim 11, wherein the combining unit comprises a mixing unit, and wherein activating the combining unit comprises activating the mixing unit to provide the solid-liquid composition by mixing the solid particles with the physiological liquid solution.

13. The method according to claim 1, wherein the solid particles are selected from the group consisting of: drug-releasing solid particles and solid drug particles, and wherein injecting comprises injecting the solid-liquid composition of the selected solid particles and the physiological liquid solution.

* * * * *

UNITED STATES PATENT AND TRADEMARK OFFICE
CERTIFICATE OF CORRECTION

PATENT NO. : 9,730,773 B2
APPLICATION NO. : 14/707688
DATED : August 15, 2017
INVENTOR(S) : Ilan Uchitel et al.

It is certified that error appears in the above-identified patent and that said Letters Patent is hereby corrected as shown below:

On the Title Page

In Page 3, Item (56), Line 55, please delete:
"2014/0147809 A1 5/2014 Uchitel et al."
And insert:
--2014/0140815 A1 5/2014 Shener-Irmakoglu et al.--

Signed and Sealed this
Third Day of October, 2017

Joseph Matal
*Performing the Functions and Duties of the*
*Under Secretary of Commerce for Intellectual Property and*
*Director of the United States Patent and Trademark Office*